United States Patent
Fischer et al.

(10) Patent No.: US 10,527,526 B2
(45) Date of Patent: Jan. 7, 2020

(54) METHODS AND COMPOSITIONS FOR PREPARING SAMPLES FOR IMMUNOSTAINING

(71) Applicant: TriPath Imaging, Inc., Burlington, NC (US)

(72) Inventors: Timothy J. Fischer, Raleigh, NC (US); Ramona R. Nelson, Durham, NC (US); Adriann J. Taylor, Durham, NC (US); Clark M. Whitehead, Cary, NC (US)

(73) Assignee: Tripath Imaging, Inc., Burlington, NC (US)

( * ) Notice: Subject to any disclaimer, the term of this patent is extended or adjusted under 35 U.S.C. 154(b) by 0 days.

(21) Appl. No.: 13/667,297

(22) Filed: Nov. 2, 2012

(65) Prior Publication Data

US 2013/0164760 A1     Jun. 27, 2013

Related U.S. Application Data

(60) Provisional application No. 61/555,139, filed on Nov. 3, 2011.

(51) Int. Cl.
    *G01N 33/569*     (2006.01)
    *G01N 33/574*     (2006.01)
    *G01N 1/30*     (2006.01)

(52) U.S. Cl.
    CPC ......... *G01N 1/30* (2013.01); *G01N 33/56966* (2013.01); *G01N 33/57492* (2013.01)

(58) Field of Classification Search
    None
    See application file for complete search history.

(56) References Cited

U.S. PATENT DOCUMENTS

| | | | |
|---|---|---|---|
| 4,619,896 A * | 10/1986 | Shattock et al. | 435/5 |
| 4,658,022 A * | 4/1987 | Knowles et al. | 530/402 |
| 5,173,422 A * | 12/1992 | Knowles et al. | 435/331 |
| 5,945,515 A | 8/1999 | Chomczynski | |
| 6,709,832 B1 | 3/2004 | Von Knebel Doeberitz et al. | |
| 6,905,858 B2 | 6/2005 | Goldstein et al. | |
| 7,157,233 B2 * | 1/2007 | Fischer et al. | 435/6.12 |
| 7,306,926 B2 | 12/2007 | Doeberitz et al. | |
| 7,510,838 B2 | 3/2009 | Fischer et al. | |
| 7,517,662 B2 | 4/2009 | Ridder et al. | |
| 7,550,298 B2 | 6/2009 | Towne et al. | |
| 7,745,145 B2 | 6/2010 | Schmitt et al. | |
| 7,927,819 B2 | 4/2011 | Schmitt et al. | |
| 2002/0094577 A1 * | 7/2002 | Guirguis | G01N 1/30 436/18 |
| 2003/0152993 A1 | 8/2003 | Doeberitz et al. | |
| 2004/0009496 A1 * | 1/2004 | Eiblmaier et al. | 435/6 |
| 2004/0265800 A1 | 12/2004 | Imoarai et al. | |
| 2005/0003462 A1 * | 1/2005 | Kaplan | 435/7.21 |
| 2005/0053607 A1 * | 3/2005 | Bates | C07K 14/47 424/155.1 |
| 2005/0260566 A1 * | 11/2005 | Fischer | C07K 16/3069 435/5 |
| 2006/0063190 A1 * | 3/2006 | Fischer | C12Q 1/6886 435/6.14 |
| 2006/0216771 A1 | 9/2006 | Doeberitz et al. | |
| 2007/0218512 A1 * | 9/2007 | Strongin et al. | 435/7.23 |
| 2008/0139800 A1 * | 6/2008 | Deggerdal et al. | 536/25.41 |
| 2008/0206772 A1 | 8/2008 | Kajita et al. | |
| 2008/0306610 A1 * | 12/2008 | Wang et al. | 623/23.72 |
| 2009/0181406 A1 | 7/2009 | Ridder et al. | |
| 2010/0008989 A1 * | 1/2010 | Attar et al. | 424/484 |
| 2010/0055695 A1 * | 3/2010 | Zichi | C12N 15/1048 435/6.12 |
| 2010/0221705 A1 * | 9/2010 | Winther | A61K 47/4823 435/6.1 |
| 2011/0065906 A1 * | 3/2011 | Liu | C12N 1/06 536/23.1 |
| 2011/0241229 A1 | 10/2011 | Naasani et al. | |
| 2015/0065383 A1 | 3/2015 | Ridder et al. | |

FOREIGN PATENT DOCUMENTS

| | | |
|---|---|---|
| EP | 2 327 987 A2 | 6/2011 |
| JP | 2005-534313 A | 11/2005 |
| JP | 2006-526591 A | 11/2006 |
| JP | 2007-206077 A | 8/2007 |
| JP | 2011-137747 A | 7/2011 |
| WO | 2004108741 A1 | 12/2004 |
| WO | WO 2011/132089 A2 | 10/2011 |

OTHER PUBLICATIONS

Yarmush, et al., Biotechnol. Prog., 8, (1992) p. 168-178.*
Jiao, et al., Journal of Neuroscience Methods, 92, (1999), p. 149-162.*
Brown et al., Histochem. Cell Biol., 105, (1996), p. 261-267.*
Larsson, L., Immunocytochemistry: Theory and Practice. Florida, CRC Press , Inc., (1988) p. 151 (3 pages).*
BD, "Material Safety Data Sheet for BD SurePath™ Preservative Fluid", retrieved from https://www.rmlonline.com/images/data/attachments/0000/1125/surepath-03-01-11-msds.pdf on Aug. 9, 2019, 7 pages total). (Year: 2011).*
Bibbo, M., et al., "P16INK4A as an Adjunct Test in Liquid-Based Cytology," *Analytical and Quantitative Cytology and Histology*, 2003, pp. 8-11, vol. 25(1).
Bibbo, M., et al., "Procedure for Immunocytochemical Detection of p16INK4A Antigen in Thin-Layer, Liquid-Based Specimens," *Acta Cytologica*, 2002, pp. 25-29, vol. 46(1).
D'Amico, F., et al., "State of the Art in Antigen Retrieval for Immunohistochemistry," *Journal of Immunological Methods*, 2009, pp. 1-18, vol. 341(1-2).
Fox, C., et al., "Formaldehyde Fixation," 1985, *J. Histochem. Cytochem.*, pp. 845-853, vol. 33(8).

(Continued)

*Primary Examiner* — Christine Foster
*Assistant Examiner* — Ellen J Marcsisin
(74) *Attorney, Agent, or Firm* — Botos Churchill IP Law LLP

(57) ABSTRACT

Compositions and methods for preparing a sample for immunological staining are provided. Compositions include kits comprising a first solution comprising a surfactant and a second solution comprising a chaotropic agent. Methods comprise contacting a sample, such as cells or tissues, with a first solution comprising a surfactant and then contacting the sample with a second solution comprising a chaotropic agent. The method does not require extreme heat for antigen retrieval and therefore, maintains the cellular morphology of the sample.

18 Claims, 4 Drawing Sheets
(4 of 4 Drawing Sheet(s) Filed in Color)

(56) References Cited

OTHER PUBLICATIONS

French, D. and J.T. Edsall, "The Reactions of Formaldehyde with Amino Acids and Proteins," *Adv. Protein Chem.*, 1945, pp. 277-335, vol. 2.

L.A.B. Product Data Sheet, "L.A.B. Solution (Liberate Antibody Binding Solution)," Polysciences, Inc., Catalog No. 24310, Technical Data Sheet 630, pp. 1-2; downloaded from world wide web at www.polysciences.com/Catalog/Department/Product/98/categoryId_634/productId_1753/ on Oct. 25, 2012.

L.A.B. Solution, Material Safety Data Sheet, Polysciences, Inc., Issue Date: Oct. 23, 2006, pp. 1-3.

Pearse, A., "Histochemistry: Theoretical and Applied, 1980," pp. 97-158, vol. 1, Churchill Livingstone, London, England.

Retrievit Product Data Sheet, "Retrievit™ Target Retrieval Solutions, Sampler Kit, 10X Concentrate," XBioGenex, Release Date: Sep. 6, 2007, pp. 1-2.

Robinson, J. and D. Vandre, "Antigen Retrieval in Cells and Tissues: Enhancement with Sodium Dodecyl Sulfate," *Histochem. Cell Biol.*, 2001, pp. 119-130, vol. 116.

Saqi, A., et al., "Overexpression of p16INK4A in Liquid-Based Specimens (SurePath™) as Marker of Cervical Dysplasia and Neoplasia," *Diagnostic Cytopathology*, 2002, pp. 365-370, vol. 27(6).

Zhang, Y. and P. Cremer, "Interactions Between Macromolecules and Ions: The Hofmeister Series," *Curr. Opin. Chem. Biol.*, 2006, pp. 658-653, vol. 10.

Japanese Office Action for Application No. 2014-540113 dated Apr. 14, 2017.

\* cited by examiner

METHODS AND COMPOSITIONS FOR PREPARING SAMPLES FOR IMMUNOSTAINING

CROSS-REFERENCE TO RELATED APPLICATIONS

This application claims the benefit of U.S. Provisional Application No. 61/555,139, filed Nov. 3, 2011, which is herein incorporated by reference in its entirety.

FIELD OF THE INVENTION

The present invention relates to methods and compositions to enhance the detection of proteins by making epitopes more accessible for antibody binding.

BACKGROUND OF THE INVENTION

Fixation of tissue and cellular samples often makes protein-based epitopes inactive, or inaccessible for immunostaining due to protein cross-linking. Antigen retrieval (AR) is the process by which target epitopes are made accessible for immunostaining. Overcoming fixation-induced cross-linking allows for target epitopes buried within the tertiary structure of proteins to become accessible for binding with primary antibodies. Antigen retrieval also advantageously lowers the threshold for detection of antigens, thereby reducing the amount of antibody needed for detection, reducing background staining, and minimizing the occurrence of false negative results. Therefore, immunohistochemistry (IHC) and immunocytochemistry (ICC) protocols often include a pretreatment step to increase the intensity of immunostaining and to retrieve the antigen of interest.

Many existing pretreatment steps for immunostaining involve the incubation of the cellular or tissue sample of interest at high temperatures of about 80° C. or greater in various solutions (e.g., buffers, EDTA, acids, bases, surfactants) to prepare the sample for immunostaining. These types of sample pretreatment methods were largely developed and optimized for processing tissue samples. Tissues can withstand the high temperature of processing and maintain morphology because these tissues are often fixed in formalin and then embedded in paraffin prior to sectioning and IHC processing, and because the tissue sections maintain the support of the surrounding stromal tissue architecture. Cytology specimens are not fixed to the same degree as tissue samples, are not normally embedded in paraffin, and do not contain stromal support material to maintain cellular morphology during high heat pretreatment. Thus, high heat pretreatment methods that serve to increase epitope exposure and accessibility to the primary antibody degrade the cellular morphology of cytology specimens.

Therefore, pretreatment methods and compositions that are effective in antigen retrieval, yet maintain cellular morphology, are needed for the processing of cytology samples, in particular, in preparation for immunostaining.

BRIEF SUMMARY OF THE INVENTION

Compositions and methods for preparing samples for immunostaining are provided herein. Compositions disclosed herein include kits comprising a first solution comprising a surfactant and a second solution comprising a chaotropic agent. The two solutions find use in retrieving protein epitopes by sequentially contacting a sample, such as cells or tissues, with the first solution and then the second solution. The exposed antigen is then available for binding to an antibody, which can be detected using any method known in the art. The presently disclosed methods and compositions allow for antigen retrieval in the absence of extreme heat, thus maintaining cellular morphology.

The following embodiments are encompassed by the present invention:

1. A kit comprising:
   a) a first solution comprising a surfactant; and
   b) a second solution comprising a chaotropic agent.
2. The kit of embodiment 1, wherein said surfactant is an anionic surfactant.
3. The kit of embodiment 2, wherein said anionic surfactant is sodium dodecyl sulfate (SDS).
4. The kit of embodiment 3, wherein said first solution comprises about 0.01% to about 1% SDS.
5. The kit of embodiment 4, wherein said first solution comprises about 0.05% to about 0.5% SDS.
6. The kit of embodiment 5, wherein said first solution comprises about 0.1% SDS.
7. The kit of any one of embodiments 1-6, wherein said first solution is an aqueous solution.
8. The kit of any one of embodiments 1-7, wherein said chaotropic agent is a chaotropic salt.
9. The kit of embodiment 8, wherein said chaotropic salt is a thiocyanate or perchlorate.
10. The kit of embodiment 9, wherein said thiocyanate is guanidine thiocyanate.
11. The kit of embodiment 10, wherein said second solution comprises about 0.3M to about 30M guanidine thiocyanate.
12. The kit of embodiment 11, wherein said second solution comprises about 1M to about 10M guanidine thiocyanate.
13. The kit of embodiment 12, wherein said second solution comprises about 3M guanidine thiocyanate.
14. The kit of embodiment 9, wherein said perchlorate is lithium perchlorate.
15. The kit of embodiment 14, wherein said second solution comprises about 0.3M to about 30M lithium perchlorate.
16. The kit of embodiment 15, wherein said second solution comprises about 1M to about 10M lithium perchlorate.
17. The kit of embodiment 16, wherein said second solution comprises about 3M lithium perchlorate.
18. The kit of any one of embodiments 1-17, wherein said second solution further comprises a weak surfactant.
19. The kit of embodiment 18, wherein said weak surfactant is a nonionic surfactant.
20. The kit of embodiment 19, wherein said weak surfactant is nonyl phenoxypolyethoxylethanol (NP-40).
21. The kit of embodiment 20, wherein said second solution comprises about 0.01% to about 1% NP-40.
22. The kit of embodiment 21, wherein said second solution comprises about 0.05% to about 0.5% NP-40.
23. The kit of embodiment 22, wherein said second solution comprises about 0.1% NP-40.
24. The kit of any one of embodiments 1-23, wherein said second solution is an aqueous solution.
25. The kit of any one of embodiments 1-24, wherein said kit further comprises an antibody that specifically binds an antigen.
26. The kit of embodiment 25, wherein said antigen is a nuclear antigen.

27. The kit of embodiment 25, wherein said antigen is selected from the group consisting of MCM2, MCM7, p16, and Ki67.

28. The kit of any one of embodiments 25-27, wherein said kit further comprises a peroxidase blocking reagent, a protein blocking reagent, chemicals for the detection of antibody binding to said antigen, a counterstain, a bluing agent, and instructions for use.

29. The kit of embodiment 28, wherein said chemicals for the detection of antibody binding comprise a chromogen and a secondary antibody conjugated to a labeled polymer, wherein the chromogen comprises 3',3'-diaminobenzidine, and wherein the labeled polymer comprises horseradish peroxidase conjugated to a dextran polymer.

30. The kit of embodiment 28 or 29, wherein said counterstain comprises hematoxylin.

31. The kit of any one of embodiments 28-30, wherein said bluing agent comprises a solution comprising Tris buffered saline, pH 7.4, Tween-20, and sodium azide.

32. The kit of any one of embodiments 25-31, further comprising a positive control sample.

33. The kit of any one of embodiments 1-32, further comprising reagents for Papanicolaou (Pap) staining.

34. The kit of embodiment 33, wherein the reagents for Pap staining comprise EA50 and Orange G.

35. A method for preparing a sample for immunological staining, said method comprising:
a) contacting the sample with a first solution comprising a surfactant; and
b) contacting the sample with a second solution comprising a chaotropic agent.

36. The method of embodiment 35, wherein said surfactant is an anionic surfactant.

37. The method of embodiment 36, wherein said anionic surfactant is sodium dodecyl sulfate (SDS).

38. The method of embodiment 37, wherein said first solution comprises about 0.01% to about 1% SDS.

39. The method of embodiment 38, wherein said first solution comprises about 0.05% to about 0.5% SDS.

40. The method of embodiment 39, wherein said first solution comprises about 0.1% SDS.

41. The method of any one of embodiments 35-40, wherein said first solution is an aqueous solution.

42. The method of any one of embodiments 35-41, wherein said chaotropic agent is a chaotropic salt.

43. The method of embodiment 42, wherein said chaotropic salt is a thiocyanate or perchlorate.

44. The method of embodiment 43, wherein said thiocyanate is guanidine thiocyanate.

45. The method of embodiment 44, wherein said second solution comprises about 0.3M to about 30M guanidine thiocyanate.

46. The method of embodiment 45, wherein said second solution comprises about 1M to about 10M guanidine thiocyanate.

47. The method of embodiment 46, wherein said second solution comprises about 3M guanidine thiocyanate.

48. The method of embodiment 43, wherein said perchlorate is lithium perchlorate.

49. The method of embodiment 48, wherein said second solution comprises about 0.3M to about 30M lithium perchlorate.

50. The method of embodiment 49, wherein said second solution comprises about 1M to about 10M lithium perchlorate.

51. The method of embodiment 50, wherein said second solution comprises about 3M lithium perchlorate.

52. The method of any one of embodiments 35-51, wherein said second solution further comprises a weak surfactant.

53. The method of embodiment 52, wherein said weak surfactant is a nonionic surfactant.

54. The method of embodiment 53, wherein said weak surfactant is nonyl phenoxypolyethoxylethanol (NP-40).

55. The method of embodiment 54, wherein said second solution comprises about 0.01% to about 1% NP-40.

56. The method of embodiment 55, wherein said second solution comprises about 0.05% to about 0.5% NP-40.

57. The method of embodiment 56, wherein said second solution comprises about 0.1% NP-40.

58. The method of any one of embodiments 35-57, wherein said second solution is an aqueous solution.

59. The method of any one of embodiments 35-58, wherein said sample is incubated with said first solution for at least one minute.

60. The method of embodiment 59, wherein said sample is incubated with said first solution for about 1 minute to about 120 minutes.

61. The method of embodiment 60, wherein said sample is incubated with said first solution for about 10 minutes to about 60 minutes.

62. The method of embodiment 61, where said sample is incubated with said first solution for about 19 minutes.

63. The method of any one of embodiments 35-62, wherein said sample is incubated in said first solution at room temperature.

64. The method of any one of embodiments 35-62, wherein said sample is heated with said first solution.

65. The method of any one of embodiments 35-62, wherein said sample is incubated with said first solution at about 20° C. to about 60° C.

66. The method of embodiment 65, wherein said sample is incubated with said first solution at about 37° C. to about 55° C.

67. The method of embodiment 66, wherein said sample is incubated with said first solution at about 50° C.

68. The method of any one of embodiments 35-67, wherein said sample is incubated with said second solution for at least one minute.

69. The method of embodiment 68, wherein said sample is incubated with said second solution for about 1 minute to about 120 minutes.

70. The method of embodiment 69, wherein said sample is incubated with said second solution for about 10 minutes to about 60 minutes.

71. The method of embodiment 70, where said sample is incubated with said second solution for about 19 minutes.

72. The method of any one of embodiments 35-71, wherein said sample is incubated with said second solution at room temperature.

73. The method of any one of embodiments 35-71, wherein said sample is heated with said second solution.

74. The method of any one of embodiments 35-71, wherein said sample is incubated with said second solution at about 30° C. to about 60° C.

75. The method of embodiment 74, wherein said sample is incubated with said second solution at about 37° C. to about 55° C.

76. The method of embodiment 75, wherein said sample is incubated with said second solution at about 50° C.

77. The method of any one of embodiments 35-76, wherein said sample is washed prior to contacting the sample with the second solution and after contacting the sample with the first solution.

78. The method of embodiment 77, wherein said sample is washed with buffered saline.

79. The method of embodiment 78, wherein said buffered saline is tris-buffered saline.

80. The method of any one of embodiments 35-79, wherein said method further comprises detecting an antigen in said sample using an antibody.

81. The method of embodiment 80, wherein said antigen is a nuclear antigen.

82. The method of embodiment 80, wherein said antigen is selected from the group consisting of MCM2, MCM7, p16, and Ki67.

83. The method of any one of embodiments 35-82, wherein said sample is a cervical sample.

84. The method of any one of embodiments 35-83, wherein said sample comprises cells or tissue.

85. The method of any one of embodiments 35-84, wherein said method further comprises performing a morphological analysis of said sample.

86. The method of any one of embodiments 35-84, wherein said method further comprises Papanicolaou (Pap) staining of the sample.

These and other aspects of the invention are disclosed in more detail in the description of the invention given below.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
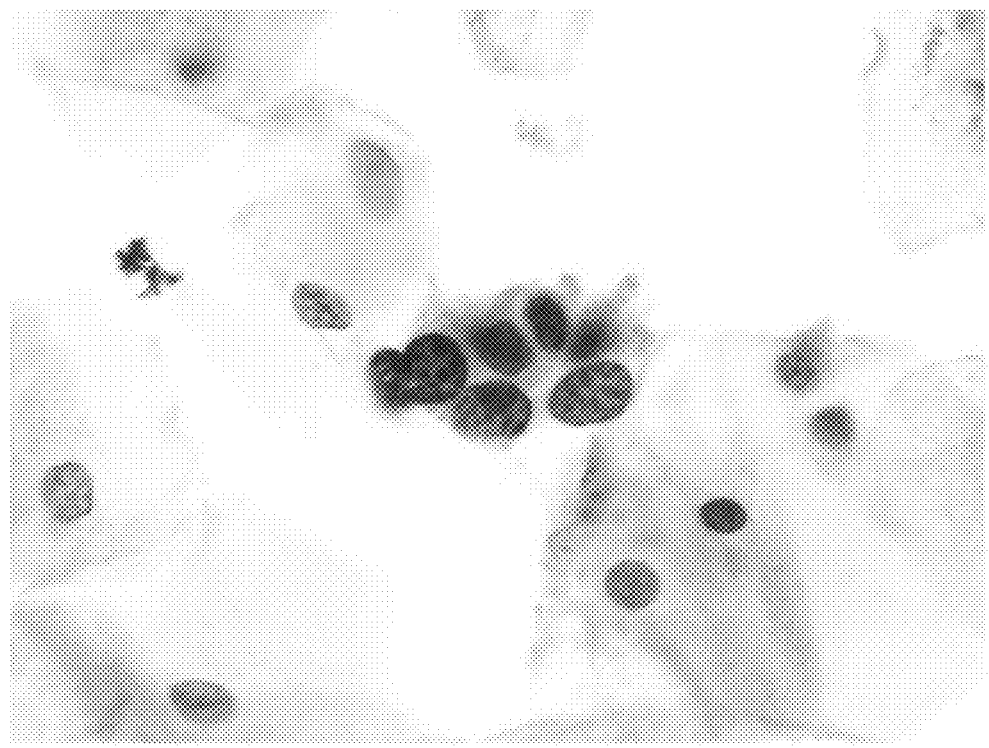
FIG. 1 provides an image of a SurePath® (TriPath Imaging, Inc.) high-grade squamous intraepithelial lesion (HSIL) cervical cytology sample immunostained with an anti-Ki67 antibody. Prior to immunostaining, the sample was incubated at 50° C. for 19 minutes in 0.1% sodium dodecyl sulfate (SDS), washed in Tris-buffered saline (TBS), and then incubated at 50° C. for 19 minutes in 3M lithium perchlorate ($LiClO_4$)/0.1% nonyl phenoxypolyethoxyl-ethanol (NP-40). The sample was counterstained with Papanicolaou (Pap) stain.

Compositions and methods are provided that are directed to preparing a sample for immunological staining by exposing protein epitopes. Compositions include kits comprising a first solution comprising a surfactant (pretreatment solution 1) and a second solution comprising a chaotropic agent (pretreatment solution 2). Methods include contacting a sample with a first pretreatment solution that comprises a surfactant and then a second pretreatment solution that comprises a chaotropic agent. Once the sample has been prepared and epitopes have been exposed, antigens can be contacted with antibodies and detected using any antigen-antibody binding detection method known in the art. The two-solution method disclosed herein allows for sufficient antigen retrieval for immunological staining in the absence of extreme heat, while maintaining cellular morphology. This is especially useful for cytology samples which are more sensitive to the extreme heat often necessary for antigen retrieval. Maintenance of cellular morphology during the antigen retrieval process is important for samples for which cellular morphology is subsequently assessed. For example, the presently disclosed compositions and methods can be used to detect antigen(s) in a cervical cytology sample in combination with standard Papinicolau counterstaining.

The presently disclosed compositions and methods are directed to preparing a sample for immunological staining. Immunological staining or immunostaining refers to the process by which a sample is contacted with at least one antibody and the binding of the antibody to its corresponding antigen within the sample is detected using any method known in the art for detecting antigen-antibody binding. Non-limiting examples of immunological staining include immunohistochemistry, wherein an antigen within a tissue sample is detected, and immunocytochemistry, wherein an antigen within a cellular sample is detected. The compositions and methods are effective in preparing samples for immunological staining, which refers to modifications of the sample to allow for access of the antibody used in the staining process to its antigen. Such modifications include permeabilization of the cytoplasmic membrane, and in some instances, the nuclear membrane, reversal of protein cross-links induced by fixatives (e.g., methylene bridges caused by aldehyde fixation; see, for example, French and Edsall (1945) *Adv Protein Chem* 2:277; Pearse (1980) Histochemistry: Theoretical and Applied vol. 1; Fox et al. (1985) *J. Histochem. Cytochem.* 33:845), and denaturation of the protein antigens. The process of preparing samples for immunological staining that allows for access of the antibody to the antigen is also referred to herein as antigen retrieval or pretreatment.

As used herein, the term "antigen" refers to a polypeptide having antigenic activity. "Antigenic activity" refers to the ability of a polypeptide to be used in the production of antibodies. The presently disclosed methods and compositions can be used to prepare samples for the detection of any type of antigen, whether it be nuclear, cytoplasmic, expressed on the cell surface, or extracellular. In some embodiments, the presently disclosed compositions and methods can be used to enhance the immunological staining of nuclear antigens and are thus capable of permeabilizing both the cytoplasmic and nuclear membranes. Non-limiting examples of nuclear antigens that can be immunostained using the presently disclosed methods include the minichromosome maintenance (MCM) proteins, such as MCM2, MCM3, MCM4, MCM5, MCM6, MCM7, and MCM10, and topoisomerase II. Non-limiting additional examples of antigens that can be immunostained using the presently disclosed methods include the estrogen receptor (ER), the progesterone receptor (PR), and p53. In some of these embodiments, the presently disclosed methods can be used to immunostain a panel of antigens including ER, PR, p53, and Ki67. In other embodiments, the presently disclosed compositions and methods are effective in enhancing the immunological staining of p16 or Ki67.

The presently disclosed compositions and methods utilize two solutions to prepare a sample for immunological staining. As used herein, the term "solution" refers to a mixture of at least two substances. The term "solution" is not limited to a homogenous mixture, but as used herein, refers to mixtures that comprise an ordered phase as well as those that comprise a more disordered phase. For example, solutions comprising a surfactant in water or another polar liquid may contain an ordered phase of micelles or a disordered phase of free surfactant molecules or ions in the solution, or a combination thereof. In some embodiments, the first or the second pretreatment solution or both pretreatment solutions are aqueous solutions. As used herein, the term "aqueous solution" refers to a mixture comprising water. In these embodiments, the surfactant or chaotropic agent, or both are dispersed or dissolved in water, which may or may not comprise additional components. In other embodiments, the surfactant or chaotropic agent, or both are dispersed or dissolved in a polar liquid other than water.

The presently disclosed compositions and methods involve a first solution that comprises a surfactant (pretreatment solution 1) and in some embodiments, the second solution (pretreatment solution 2) also comprises a surfactant. As used herein, the terms "surfactant," "surface-active agent," and "detergent" can be used interchangeably herein and refer to molecules that can reduce the surface tension of a liquid. Surfactants have both hydrophilic and hydrophobic properties, and thus, can be solubilized to some extent in either water or nonpolar solvents. Surfactants are classified into four primary groups: cationic, anionic, non-ionic, and zwitterionic. Without being bound by any theory or mechanism of action, it is believed that the presence of a surfactant in the first pretreatment solution, and in some embodiments in the second pretreatment solution, contributes to the permeabilization of the cytoplasmic and in some instances, nuclear membranes. Further, surfactants, such as sodium dodecyl sulfate (SDS), also penetrate the hydrophobic interior of proteins and equilibrate the charge distribution of proteins, thereby denaturing proteins and increasing epitope exposure and accessibility to the primary antibody.

In some embodiments of the presently disclosed methods and compositions, the first pretreatment solution comprises an anionic surfactant. Anionic surfactants are those surfactants that have a net negative charge when dissolved or dispersed in aqueous solutions. Representative, non-limiting examples of anionic surfactants include alkyl sulfates, such as ammonium lauryl sulfate and sodium dodecyl sulfate (SDS); alkyl ether sulfates, such as sodium laureth sulfate and sodium myreth sulfate; docusates, such as dioctyl sodium sulfosuccinate; sulfonate fluorosurfactants, such as perfluorooctanesulfonate and perfluorobutanesulfonate; alkyl benzene sulfonates; alkyl aryl ether phosphate; alkyl ether phosphate; alkyl carboxylates, such as fatty acid salts, and sodium stearate; sodium lauroyl sarcosinate; carboxylate fluorosurfactants, such as perfluorononanoate and perfluorooctanoate; alkyl sulfate esters, such as sodium cetyl sulfate; alkyl sulfonates, such as sodium dodecyl sulfonate and alkyl allyl sulfonates; sodium stearate; sodium deoxycholate; and sodium lauroyl sarcosinate.

In other embodiments, the surfactant in the first pretreatment solution is cationic (i.e., has a net positive charge when dissolved or dispersed in aqueous solutions), nonionic (i.e., has no charge when dissolved or dispersed in aqueous solutions), or zwitterionic (i.e., has a net neutral charge when dissolved or dispersed in aqueous solutions, but has both a negative and positive electrical charge at different locations within the surfactant molecule).

In certain embodiments, the first pretreatment solution comprises sodium dodecyl sulfate (SDS), which is also referred to as sodium laurilsulfate or sodium lauryl sulfate (SLS). SDS consists of a twelve carbon tail attached to a sulfate group and has the molecular formula $NaC_{12}H_{25}SO_4$. In some of these embodiments, the first pretreatment solution comprises about 0.001% to about 10% SDS, including but not limited to about 0.001%, about 0.05%, about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, and other such values between about 0.001% and about 10% SDS. In certain embodiments, the first pretreatment solution comprises about 0.01% to about 1% SDS. In other embodiments, the first pretreatment solution comprises about 0.05% to about 0.5% SDS. In some of these embodiments, the first pretreatment solution comprises about 0.1% SDS.

The second pretreatment solution utilized in the presently disclosed compositions and methods comprises a chaotropic agent. As used herein, the term "chaotropic agent" refers to a substance that has the ability to destabilize intramolecular interactions mediated by non-covalent forces, such as hydrogen bonds, van der Waals forces, and hydrophobic interactions, which allows for nonpolar compounds, such as proteins, to dissolve more readily in aqueous solutions. Without being bound by any theory or mechanism of action, it is believed that the chaotropic agent in the second pretreatment solution contributes to the dissolution of biological membranes and the denaturation of proteins by allowing water molecules to penetrate into the interior of proteins and solvate nonpolar side chains, thereby disrupting the hydrophobic interactions that normally stabilize the native conformation. Non-limiting examples of chaotropic agents suitable for use in the presently disclosed methods and compositions include chaotropic salts, urea, and thiourea.

In some embodiments, the second pretreatment solution comprises a chaotropic salt. As used herein, the term "chaotropic salt" refers to an ionic compound comprised of cations and anions that can function as a chaotropic agent as defined elsewhere herein. In general, it is the anion of the salt that contributes to the chaotropic properties of a chaotropic salt. The position of an ion in the Hofmeister series (see, for example, Hofmeister (1888) *Arch. Exp. Pathol. Pharmacol.* 24:247-260; Zhang and Cremer (2006) *Curr Opin Chem Biol* 10:658-663, each of which are incorporated herein in its entirety), which orders ions based on their ability to solvate proteins, can be used to select a chaotropic salt for use in the presently disclosed compositions and methods. Ions that appear late in the Hofmeister series, such as $SCN^-$, $ClO_4^-$, $I^-$, $ClO_3^-$, and $Br^-$, would be expected to have greater chaotropic properties. Thus, in some embodiments, the chaotropic salt comprises an anion selected from the group consisting of $SCN^-$ (thiocyanate), $CNS^-$, $ClO_3^-$, $ClO_4^-$ (perchlorate), $I^-$, $Br^-$, $NO_3^-$, $Cl^-$, $CH_3CO_2^-$ (acetate). Representative non-limiting examples of chaotropic salts suitable for use in the presently disclosed methods and compositions include guanidine hydrochloride, guanidine thiocyanate, and lithium perchlorate.

In particular embodiments, the chaotropic salt is a thiocyanate or perchlorate, which refers to a salt comprising cations and anions, wherein the anion is thiocyanate ($SCN^-$) or perchlorate ($ClO4^-$). In some of these embodiments, the chaotropic salt is a perchlorate. Non-limiting examples of perchlorates suitable for use in the presently disclosed methods and compositions include ammonium perchlorate ($NH_4ClO_4$), cesium perchlorate ($CsClO_4$), lithium perchlorate ($LiClO_4$), magnesium perchlorate ($Mg(ClO_4)_2$), potassium perchlorate ($KClO_4$), rubidium perchlorate ($RbClO_4$), silver perchlorate ($AgClO_4$), perchloric acid ($HClO_4$), calcium perchlorate ($Ca(ClO_4)_2$), and sodium perchlorate ($NaClO_4$). In certain embodiments, the chaotropic salt in the second pretreatment solution is lithium perchlorate (LiClO4).

In some of those embodiments wherein the second pretreatment solution comprises lithium perchlorate, lithium perchlorate is present within the second pretreatment solution at a concentration of about 0.3M to about 30M, including but not limited to about 0.3M, about 0.4M, about 0.5M, about 0.6M, about 0.7M, about 0.8M, about 0.9M, about 1M, about 2M, about 3M, about 4M, about 5M, about 6M, about 7M, about 8M, about 9M, about 10M, about 11M, about 12M, about 13M, about 14M, about 15M, about 16M, about 17M, about 18M, about 19M, about 20M, about 21M, about 22M, about 23M, about 24M, about 25M, about 26M, about 27M, about 28M, about 29M, and about 30M. In certain embodiments, the second pretreatment solution comprises about 1M to about 10M lithium perchlorate. In some of these embodiments, the second pretreatment solution comprises about 3M lithium perchlorate.

In other embodiments, the chaotropic salt present in the second pretreatment solution is a thiocyanate. Non-limiting examples of thiocyanates suitable for use in the presently disclosed methods and compositions include potassium thiocyanate (KSCN), sodium thiocyanate (NaSCN), ammonium thiocyanate ($NH_4SCN$), and guanidine thiocyanate ($C_2H_6N_4S$; also referred to as guanidinium thiocyanate). In certain embodiments, the chaotropic salt is guanidine thiocyanate, which is comprised of the guanidinium cation ($CH_6N_3^+$) and the thiocyanate anion ($SCN^-$).

In some of those embodiments wherein the second pretreatment solution comprises guanidine thiocyanate, guanidine thiocyanate is present within the second pretreatment solution at a concentration of about 0.3M to about 30M, including but not limited to about 0.3M, about 0.4M, about 0.5M, about 0.6M, about 0.7M, about 0.8M, about 0.9M, about 1M, about 2M, about 3M, about 4M, about 5M, about 6M, about 7M, about 8M, about 9M, about 10M, about 11M, about 12M, about 13M, about 14M, about 15M, about 16M, about 17M, about 18M, about 19M, about 20M, about 21M, about 22M, about 23M, about 24M, about 25M, about 26M, about 27M, about 28M, about 29M, about 30M, and other such values between about 0.3M and about 30M. In certain embodiments, the second pretreatment solution comprises about 1M to about 10M guanidine thiocyanate. In some of these embodiments, the second pretreatment solution comprises about 3M guanidine thiocyanate.

In certain embodiments, in addition to the chaotropic agent, the second pretreatment solution comprises a weak surfactant. As used herein, the term "weak surfactant" refers to a surfactant or concentration of a surfactant that is capable of lysing mammalian cells, but maintains or has a minimal effect on cellular morphology. Non-limiting examples of weak surfactants include nonionic or zwitterionic surfactants. Alternatively, a weak surfactant can be a surfactant molecule that is capable of changing cellular morphology at some concentrations (e.g., anionic surfactant), but is present in the second pretreatment solution at a low enough concentration such that the surfactant has minimal effect on cellular morphology.

Zwitterionic surfactants are those surfactants that have a net neutral charge when dissolved or dispersed in aqueous solutions, but have both a negative and positive electrical charge at different locations within the surfactant molecule. Representative non-limiting examples of zwitterionic surfactants suitable for use in the presently disclosed methods and compositions include those that are based on primary, secondary, or tertiary amines or quaternary ammonium cations paired with sulfonates, such as 3-[(3-cholamidopropyl)dimethylammonio]-1-propane sulfonate (CHAPS); carboxylates, such as betaines and amino acids; or phosphates, such as lecithin.

Non-ionic surfactants are those surfactants that have no charge when dissolved or dispersed in aqueous solutions. Representative non-limiting examples of non-ionic surfactants suitable for use in the presently disclosed methods and compositions include polysorbates, including but not limited to, polyethoxylated sorbitan fatty acid esters (e.g., Tween® compounds), such as polyoxyethylene (POE) sorbitan monooleate (Tween® 80), POE sorbitan monostearate (Tween® 60), POE sorbitan monolaurate (Tween® 20), and POE sorbitan monopalmitate (Tween® 40); sorbitan derivatives (e.g., Span® compounds); ethylene oxide/propylene oxide copolymers (e.g., Pluronic® compounds, which are also known as poloxamers); polyoxyethylene ether compounds, such as those of the Brij® family, including but not limited to polyoxyethylene stearyl ether (also known as polyoxyethylene (100) stearyl ether and by the trade name Brij® 700); polyoxyethylene glycol octylphenol ethers, such as polyoxyethylene p-t-octyl phenol (Triton X-1000®);

polyoxypropylene glycol alkyl ethers; glucoside alkyl ethers, such as octyl glucoside; glycerol alkyl ethers; polyoxyethylene glycol alkylphenol ethers; nonyl phenoxylpolyethoxylethanol (NP-40; also known as Tergitol® type NP-40); and ethers of fatty alcohols.

In some embodiments, the second pretreatment solution comprises nonylphenol ethoxylate (NP-40). In some of those embodiments wherein the second pretreatment solution comprises NP-40, NP-40 is present within the second pretreatment solution at a concentration of about 0.001% to about 10%, including but not limited to about 0.001%, about 0.05%, about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, and other such values between about 0.001% and about 10%. In certain embodiments, the second pretreatment solution comprises about 0.01% to about 1% NP-40. In other embodiments, the second pretreatment solution comprises about 0.05% to about 0.5% NP-40. In some of these embodiments, the second pretreatment solution comprises about 0.1% NP-40.

Thus, in some embodiments, the second pretreatment solution comprises an aqueous solution of about 3 M lithium perchlorate or guanidine thiocyanate and about 0.1% NP-40. In some of these embodiments, this second pretreatment solution is used in combination with a first pretreatment solution that comprises an aqueous solution of about 0.1% SDS for preparing samples for immunological staining.

The two presently disclosed pretreatment solutions find use in preparing samples for immunological staining. As used herein, the term "sample" refers to a biological sample or a sample obtained from a biological material in which expression of a protein can be detected. Non-limiting examples of biological samples include cells (including cytology samples and cultured cells), tissues, biopsies, smears, and bodily fluids, such as blood, lymph, urine, saliva, and gynecological fluids. Biological samples may be obtained from a patient by a variety of techniques including, for example, by lavage, scraping or swabbing an area or by using a needle to aspirate bodily fluids. Methods for collecting various biological samples are well known in the art.

The sample may be unfixed or fixed using any method or fixative known in the art. Non-limiting examples of fixatives suitable for use in the presently disclosed compositions and methods include cross-linking fixatives, such as aldehydes (e.g., formaldehyde, glutaraldehyde, formalin), which create covalent chemical bonds between proteins through the formation of methylene bridges (see, for example, French and Edsall (1945) *Adv Protein Chem* 2:277; Pearse (1980) Histochemistry: Theoretical and Applied vol. 1; Fox et al. (1985) *J. Histochem. Cytochem.* 33:845); precipitating fixatives, such as alcohols (e.g., ethanol, methanol) and acetone; oxidizing agents, such as osmium tetroxide, potassium dichromate, chromic acid, and potassium permanganate; mercurial, such as B-5 and Zenker's; and picrates.

In some embodiments, the sample comprises a tissue sample. Tissue samples can be prepared using any method known in the art, including freezing or embedding the tissue in paraffin or an epoxy or acrylic resin prior to sectioning. In certain embodiments, the tissue sample is fixed in a solution comprising about 10% formaldehyde for about 24 hours prior to sectioning.

In particular embodiments, the sample comprises cervical cells, as cervical tissue samples or as cervical cells in suspension, particularly in a liquid-based preparation. In some embodiments, cervical samples are collected according to liquid-based cytology specimen preparation guidelines such as, for example, the SurePath® (TriPath Imaging, Inc.) or the ThinPrep® preparation (CYTYC, Inc.). Cervical samples may be transferred to a glass slide for viewing under magnification. In some of these embodiments, a patient cervical sample is collected into a liquid medium, such as, for example, in a SurePath™ collection vial (TriPath Imaging, Inc.). An automated processor such as the PrepStain™ system (TriPath Imaging, Inc.) is used to collect cells from the liquid medium and to deposit them in a monolayer on a glass slide for further analysis.

In one embodiment the cervical sample will be collected and processed to provide a monolayer sample, as set forth in U.S. Pat. No. 5,346,831, herein incorporated by reference. The monolayer method relates to a method for producing a monolayer of cytological material on a cationically-charged substrate. The method comprises the steps of separating the cytological material by centrifugation over a density gradient, producing a packed pellet of the cytological material, mixing the pellet of the cytological material, withdrawing an aliquot of a predetermined volume from the mixed pellet, depositing the aliquot and a predetermined volume of water into a sedimentation vessel, which is removably secured to the cationically-charged substrate, allowing the cytological material to settle onto the substrate under the force of gravity, and after settlement of the cytological material, removing the water from the sedimentation vessel. For automated analysis, the sedimentation vessel may be detached from the substrate. Disaggregation may be by any method known in the art, such as syringing, trypsinizing, ultrasonication, shaking, vortexing, or by use of the device described in U.S. Pat. No. 5,316,814, the contents of which are herein incorporated by reference.

Slide specimens may be fixed or unfixed and may be analyzed immediately following preparation or may be stored for later analysis. In some embodiments, prepared slides are stored in about 95% ethanol for a minimum of 24 hours. Alternatively, in other embodiments, slides are stored in the first pretreatment solution disclosed herein (i.e., a solution comprising a surfactant).

According to the presently disclosed methods for preparing a sample for immunological staining, the sample is first contacted with the first pretreatment solution that comprises a surfactant, and then with the second pretreatment solution that comprises a chaotropic agent, and in some embodiments, a weak surfactant. The sample can be contacted with the presently disclosed pretreatment solutions using any method that results in the sample coming into contact with the solution. Therefore, in some embodiments, the pretreatment solution can be added to the sample in such a manner as to cover the sample with the solution. Alternatively, the sample can be added to the pretreatment solution, and in some embodiments, the sample can be submersed in the solution.

In some embodiments, the sample is incubated with the first pretreatment solution for at least one minute. In other embodiments, the sample is incubated with the first pretreatment solution for about 1 minute to about 120 minutes, including but not limited to, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 30, about 40, about 50, about 60, about 70, about 80, about 90, about 100, about 110, about 120 minutes, and other such values between about 1 minute and about 120 minutes. In particular embodiments, the sample is incubated with the first pretreatment solution for about 10 minutes to about 60 minutes. In some of these embodiments, the sample is incubated with the first pretreatment solution comprising a surfactant for about 19 minutes.

In other embodiments, the first pretreatment solution may also serve as a storage buffer for a sample, particularly a sample that has been fixed, wherein the sample is stored in the first pretreatment solution for at least about 24 hours, about 48 hours, about 72 hours, about 4 days, about 5 days, about 7 days, about 2 weeks, about a month, about 1 year, or greater.

The sample can be incubated in the first pretreatment solution at room temperature or heat can be applied. Thus, in some embodiments, the incubation temperature of the sample in the first pretreatment solution is about 20° C. to about 60° C., including but not limited to about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., about 50° C., about 51° C., about 52° C., about 53° C., about 54° C., about 55° C., about 56° C., about 57° C., about 58° C., about 59° C., about 60° C., and other such values between about 20° C. and about 60° C. In certain embodiments, the sample is incubated with the first pretreatment solution at a temperature of about 37° C. to about 55° C. In some of these embodiments, the incubation temperature is about 50° C.

In particular embodiments, the sample is incubated with the first pretreatment solution at about 50° C. for about 19 minutes. In some of these embodiments, the first pretreatment solution is an aqueous solution comprising about 0.1% SDS.

Following the incubation of the sample in the first pretreatment solution that comprises a surfactant, the sample is contacted with a second pretreatment solution that comprises a chaotropic agent, and in some embodiments, a weak surfactant. This can be accomplished by removing the sample from the first pretreatment solution or removing the solution from the sample and then transferring the sample to the second pretreatment solution or applying the second solution to the sample. Following removal of the first pretreatment solution from the sample or the sample from the first pretreatment solution, the sample can be washed to remove the residual first pretreatment solution prior to contacting the sample with the second pretreatment solution.

As used herein, the term "wash" as it relates to a sample refers to transiently contacting the sample with another solution, other than the first or second pretreatment solutions to remove traces of the active component of the pretreatment solution (e.g., surfactant, chaotropic agent). In some embodiments, the wash solution is water or a buffered saline. Various buffered salines used for cellular and molecular biological methods are known in the art and include, but are not limited to, phosphate-buffered saline (PBS), HEPES-buffered saline, and tris-buffered saline (TBS). In some embodiments, the sample is washed with tris-buffered saline after removal of the first pretreatment solution and prior to contacting the sample with the second pretreatment solution. The sample may be washed one or more times with the wash solution.

The sample is then contacted with the second pretreatment solution that comprises a chaotropic agent and in some embodiments, a weak surfactant. In some embodiments, the sample is incubated with the second pretreatment solution for at least one minute. In other embodiments, the solution is incubated with the second pretreatment solution for about 1 minute to about 120 minutes, including but not limited to, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 30, about 40, about 50, about 60, about 70, about 80, about 90, about 100, about 110, about 120 minutes, and other such values between about 1 minute and about 120 minutes. In particular embodiments, the sample is incubated with the second pretreatment solution for about 10 minutes to about 60 minutes. In some of these embodiments, the sample is incubated with the second pretreatment solution for about 19 minutes.

The sample can be incubated in the second pretreatment solution at room temperature or heat can be applied. Thus, in some embodiments, the incubation temperature of the sample in the second pretreatment solution is about 20° C. to about 60° C., including but not limited to about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., about 50° C., about 51° C., about 52° C., about 53° C., about 54° C., about 55° C., about 56° C., about 57° C., about 58° C., about 59° C., about 60° C., and other such values between about 20° C. and about 60° C. In certain embodiments, the sample is incubated with the second pretreatment solution at a temperature of about 37° C. to about 55° C. In some of these embodiments, the incubation temperature is about 50° C.

In particular embodiments, the sample is incubated with the second pretreatment solution at about 50° C. for about 19 minutes. In some of these embodiments, the sample has been incubated with the first pretreatment solution at about 50° C. for about 19 minutes prior to incubation with the second pretreatment solution.

One of skill in the art will recognize that the incubation temperature and time period of the incubation with the first, second, or first and second pretreatment solutions will vary depending upon the type of sample being prepared for immunostaining and the extent to which the sample has been fixed. For example, those samples that have been fixed with a cross-linking fixative might require a higher temperature or longer incubation period with the first, second, or first and second pretreatment solutions when compared to a sample that has been fixed with alcohol. Further, a paraffin-embedded tissue sample might be able to withstand greater incubation temperatures and longer incubation periods with the first, second, or first and second pretreatment solutions than a cytology sample, without affecting cellular morphology.

Once the sample has been prepared by contacting the sample with the first and second pretreatment solutions, the method can further comprise using any method known in the art to detect an antigen in the prepared sample using an antibody. The terms "antibody" and "antibodies" broadly encompass naturally occurring forms of antibodies and recombinant antibodies such as single-chain antibodies, chimeric and humanized antibodies and multi-specific antibodies as well as fragments and derivatives of all of the foregoing, which fragments and derivatives have at least an antigenic binding site. Antibody derivatives may comprise a protein or chemical moiety conjugated to the antibody.

"Antibodies" and "immunoglobulins" (Igs) are glycoproteins having the same structural characteristics. While antibodies exhibit binding specificity to an antigen, immunoglobulins include both antibodies and other antibody-like molecules that lack antigen specificity. Polypeptides of the latter kind are, for example, produced at low levels by the lymph system and at increased levels by myelomas.

The term "antibody" is used in the broadest sense and covers fully assembled antibodies, antibody fragments that can bind antigen (e.g., Fab', F'(ab)$_2$, Fv, single chain antibodies, diabodies), and recombinant peptides comprising the foregoing.

The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Antibody fragments" comprise a portion of an intact antibody, preferably the antigen-binding or variable region of the intact antibody. Examples of antibody fragments include Fab, Fab', F(ab')2, and Fv fragments; diabodies; linear antibodies (Zapata et al. (1995) *Protein Eng.* 8(10): 1057-1062); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize 35 readily. Pepsin treatment yields an F(ab')2 fragment that has two antigen-combining sites and is still capable of cross-linking antigen.

"Fv" is the minimum antibody fragment that contains a complete antigen recognition and binding site. In a two-chain Fv species, this region consists of a dimer of one heavy- and one light-chain variable domain in tight, non-covalent association. In a single-chain Fv species, one heavy- and one light-chain variable domain can be covalently linked by flexible peptide linker such that the light and heavy chains can associate in a "dimeric" structure analogous to that in a two-chain Fv species. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain ($C_H1$) of the heavy chain. Fab fragments differ from Fab' fragments by the addition of a few residues at the carboxy terminus of the heavy-chain $C_H1$ domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments that have hinge cysteines between them.

Polyclonal antibodies can be prepared by immunizing a suitable subject (e.g., rabbit, goat, mouse, or other mammal) with a protein immunogen. The antibody titer in the immunized subject can be monitored over time by standard techniques, such as with an enzyme linked immunosorbent assay (ELISA) using immobilized protein. At an appropriate time after immunization, e.g., when the antibody titers are highest, antibody-producing cells can be obtained from the subject and used to prepare monoclonal antibodies by standard techniques, such as the hybridoma technique originally described by Kohler and Milstein (1975) *Nature* 256:495-497, the human B cell hybridoma technique (Kozbor et al. (1983) *Immunol. Today* 4:72), the EBV-hybridoma technique (Cole et al. (1985) in *Monoclonal Antibodies and Cancer Therapy*, ed. Reisfeld and Sell (Alan R. Liss, Inc., New York, N.Y.), pp. 77-96) or trioma techniques. The technology for producing hybridomas is well known (see generally Coligan et al., eds. (1994) *Current Protocols in Immunology* (John Wiley & Sons, Inc., New York, N.Y.); Galfre et al. (1977) *Nature* 266:550-52; Kenneth (1980) in *Monoclonal Antibodies: A New Dimension In Biological Analyses* (Plenum Publishing Corp., NY); and Lerner (1981) *Yale J. Biol. Med.*, 54:387-402).

As an alternative to preparing monoclonal antibody-secreting hybridomas, a monoclonal antibody can be identified and isolated by screening a recombinant combinatorial immunoglobulin library (e.g., an antibody phage display library) with a protein of interest to thereby isolate immunoglobulin library members that bind to the protein of interest. Kits for generating and screening phage display libraries are commercially available (e.g., the Pharmacia Recombinant Phage Antibody System, Catalog No. 27-9400-01; and the Stratagene SurfZAP ϑ Phage Display Kit, Catalog No. 240612). Additionally, examples of methods and reagents particularly amenable for use in generating and screening antibody display library can be found in, for example, U.S. Pat. No. 5,223,409; PCT Publication Nos. WO 92/18619; WO 91/17271; WO 92/20791; WO 92/15679; 93/01288; WO 92/01047; 92/09690; and 90/02809; Fuchs et al. (1991) *Bio/Technology* 9:1370-1372; Hay et al. (1992) *Hum. Antibod. Hybridomas* 3:81-85; Huse et al. (1989) *Science* 246:1275-1281; Griffiths et al. (1993) *EMBO J.* 12:725-734.

Following incubation of the sample with the first and second pretreatment solutions and prior to incubation with an antibody, samples can be blocked using an appropriate blocking agent, e.g., a peroxidase blocking reagent such as hydrogen peroxide. In some embodiments, the samples are blocked using a protein blocking reagent to prevent non-specific binding of the antibody. The protein blocking reagent may comprise, for example, purified casein.

An antibody, particularly a monoclonal antibody, directed to an antigen of interest is then incubated with the sample. More than one antibody may be used in the immunostaining procedure. Where more than one antibody is used, these antibodies may be added to a single sample sequentially as individual antibody reagents or simultaneously as an antibody cocktail. Alternatively, each individual antibody may be added to a separate sample from the same patient, and the resulting data pooled.

Techniques for detecting antibody binding are well known in the art. Antibody binding to an antigen of interest may be detected through the use of chemical reagents that generate a detectable signal that corresponds to the level of antibody binding and, accordingly, to the level of expression of the antigen. Non-limiting examples of detectable substances that can be used to detect antigen-antibody binding include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{35}$S, or $^{3}$H.

In some embodiments, antibody binding is detected through the use of a secondary antibody that is conjugated to a labeled polymer. Examples of labeled polymers include but are not limited to polymer-enzyme conjugates. The enzymes in these complexes are typically used to catalyze the deposition of a chromogen at the antigen-antibody binding site, thereby resulting in cell staining that corresponds to expression level of the antigen of interest. Enzymes of particular interest include horseradish peroxidase (HRP) and alkaline phosphatase (AP). Commercial antibody detection systems, such as, for example the Dako Envision+ system and Biocare Medical's Mach 3 system, may be used to practice the present invention.

In particular embodiments, antibody binding to an antigen is detected through the use of an HRP-labeled polymer that is conjugated to a secondary antibody. Antibody binding can also be detected through the use of a mouse probe reagent, which binds to mouse monoclonal antibodies, and a polymer conjugated to HRP, which binds to the mouse probe reagent. Samples are stained for antibody binding using the chromogen 3,3-diaminobenzidine (DAB) and then counterstained with hematoxylin and, optionally, a bluing agent such as ammonium hydroxide or TBS/Tween-20. In some aspects of the invention, samples are reviewed microscopically by a cytotechnologist and/or a pathologist to assess cell staining. Alternatively, samples may be reviewed via automated microscopy or by personnel with the assistance of computer software that facilitates the identification of positive staining cells.

In regard to detection of antibody staining, there also exist in the art, video-microscopy and software methods for the quantitative determination of an amount of multiple molecular species in a biological sample wherein each molecular species present is indicated by a representative dye marker having a specific color. Such methods are also known in the art as a colorimetric analysis methods. In these methods, video-microscopy is used to provide an image of the sample after it has been stained to visually indicate the presence of a particular antigen of interest. Some of these methods, such as those disclosed in U.S. patent application Ser. No. 09/957,446 to Marcelpoil et al. and U.S. patent application Ser. No. 10/057,729 to Marcelpoil et al., incorporated herein by reference, disclose the use of an imaging system and associated software to determine the relative amounts of each molecular species present based on the presence of representative color dye markers as indicated by those color dye markers' optical density or transmittance value, respectively, as determined by an imaging system and associated software. These techniques provide quantitative determinations of the relative amounts of each molecular species in a stained biological sample using a single video image that is "deconstructed" into its component color parts.

Furthermore, the location of antigens within the cell is also an important consideration in immunological staining methods. Proteins that display nuclear, cytoplasmic, or membrane staining patterns can be confirmed morphologically and are appropriate for immunohistochemistry methods. Cytoplasmic and membrane staining, however, make it difficult to identify critical morphological characteristics of cervical disease (e.g., nuclear to cytoplasmic ratio) in immunocytochemistry assays. In contrast, proteins that are expressed in the nucleus and show a nuclear staining pattern facilitate detection of antibody staining and also permit morphological analysis. Thus, in some embodiments, only proteins that are selectively expressed in the nucleus are detected using the presently disclosed pretreatment and immunostaining procedures.

One of skill in the art will recognize that optimization of antibody titer and detection chemistry is needed to maximize the signal to noise ratio for a particular antibody. Antibody concentrations that maximize specific binding to an antigen of interest and minimize non-specific binding (or "background") will be determined. The design of assays to optimize antibody titer and detection conditions is standard and well within the routine capabilities of those of ordinary skill in the art.

Furthermore, one of skill in the art will recognize that the concentration of a particular antibody used to practice the presently disclosed methods will vary depending on such factors as time for binding and the level of specificity of the antibody for its antigen. Moreover, when multiple antibodies are used, the required concentration may be affected by the order in which the antibodies are applied to the sample, i.e., simultaneously as a cocktail or sequentially as individual antibody reagents. Furthermore, the detection chemistry used to visualize antibody binding to an antigen of interest must also be optimized to produce the desired signal to noise ratio.

The presently disclosed pretreatment methods allow for the maintenance of cellular morphology of the samples. Therefore, in some embodiments, the morphological characteristics of the sample can be assessed. For example, immunostaining can be combined with the conventional Pap stain so that all the morphological information from the conventional method is conserved. In this manner, the detection of specific biomarkers such as those disclosed in U.S. Pat. No. 7,510,838, which is herein incorporated by reference in its entirety, can reduce the high false-negative rate of the Pap smear test and may facilitate mass automated screening. In some embodiments, the immunostaining procedure is combined with the conventional Pap stain in a single method. A combined immunocytochemistry and Pap staining method permits visualization of both biomarkers that are selectively overexpressed in high-grade cervical disease and cell morphology in a single sample (e.g., a microscope slide comprising a monolayer of cervical cells). The combined immunocytochemistry and Pap staining method may permit the more accurate identification and diagnosis of high-grade cervical disease, particularly in cases mistakenly classified as normal, LSIL, or ASCUS by conventional Pap testing.

One of skill in the art will recognize that the staining parameters (e.g., incubation times, wash conditions, chromogen/stain concentrations, etc.) for this combined methodology will need to be optimized such that a sufficient contrast between the immunostaining output (e.g., chromogen staining) and the Pap stain is obtained. The design of assays to optimize staining parameters is standard and well within the routine capabilities of those of ordinary skill in the art.

One of skill in the art will further appreciate that any or all steps in the methods of the invention could be implemented by personnel or, alternatively, performed in an automated fashion using, for example, the Autostainer Universal Staining System (Dako) or the Biocare Nemesis Autostainer (Biocare). Thus, the steps of sample preparation, sample staining, and detection of antigen expression may be automated.

The presently disclosed compositions include kits for practicing the presently disclosed immunostaining pretreatment methods. These kits comprise a first solution that comprises a surfactant (which in some embodiments is an anionic surfactant, such as SDS), and a second solution that comprises a chaotropic agent (which in some embodiments is a thiocyanate, such as guanidine thiocyanate, or a perchlorate, such as lithium perchlorate) and in some embodiments, a weak surfactant (e.g., NP-40).

In some embodiments, the kits further comprise an antibody that specifically binds an antigen. In some of these embodiments, the kits further comprise more than one antibody that specifically detects the expression of at least two distinct antigens. Each antibody may be provided in the kit as an individual reagent or, alternatively, as an antibody cocktail comprising all of the antibodies directed to the different antigens of interest.

The kit can further comprise chemicals for the detection of antibody binding to the antigen, and in some embodiments, a counterstain, and, optionally, a bluing agent to facilitate identification of positive staining cells. In one embodiment, the kit comprises a secondary antibody that is conjugated to an HRP-labeled polymer. Chromogens compatible with the conjugated enzyme (e.g., DAB in the case of an HRP-labeled secondary antibody) and solutions, such as hydrogen peroxide, for blocking non-specific staining may be further provided. In other embodiments, antibody binding to an antigen is detected through the use of a mouse probe reagent that binds to mouse monoclonal antibodies, followed by addition of a dextran polymer conjugated with HRP that binds to the mouse probe reagent. Such detection reagents are commercially available from, for example, Biocare Medical.

The kits of the present invention may further comprise a peroxidase blocking reagent (e.g., hydrogen peroxide), a protein blocking reagent (e.g., purified casein), and a counterstain (e.g., hematoxylin). A bluing agent (e.g., ammonium hydroxide or TBS, pH 7.4, with Tween-20 and sodium azide) may be further provided in the kit to facilitate detection of positive staining cells.

Positive and/or negative controls may be included in the kits to validate the activity and correct usage of reagents employed in accordance with the invention. Controls may include samples, such as tissue sections, cells fixed on glass slides, etc., known to be either positive or negative for the presence of the antigen of interest. In a particular embodiment, the positive control comprises SiHa cells. This is a human cervical squamous cancer cell line that is hypertriploid and positive for HPV-16 infection and, therefore, serves as a positive control for the overexpression of biomarkers in high-grade cervical disease states. SiHa control cells may be provided in the presently disclosed kits as prepared slides or as a cell suspension that is compatible with slide preparation. The design and use of controls is standard and well within the routine capabilities of those of ordinary skill in the art.

Kits for performing the presently disclosed pretreatment methods and the combined immunostaining and Pap staining method are also encompassed by the present invention. Such kits comprise the reagents needed for the pretreatment step, the immunostaining procedure, as described herein above, and the reagents for conventional Pap staining, particularly EA50 and Orange G.

Presently disclosed kits are compatible with both manual and automated pretreatment and immunostaining techniques. Any or all of the kit reagents may be provided within containers that protect them from the external environment, such as in sealed containers.

It is to be noted that the term "a" or "an" entity refers to one or more of that entity; for example, "an antibody" is understood to represent one or more antibodies. As such, the terms "a" (or "an"), "one or more," and "at least one" can be used interchangeably herein.

Throughout this specification and the claims, the words "comprise," "comprises," and "comprising" are used in a non-exclusive sense, except where the context requires otherwise.

As used herein, the term "about," when referring to a value is meant to encompass variations of, in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the presently disclosed subject matter be limited to the specific values recited when defining a range.

Unless defined otherwise, all technical and scientific terms used herein have the same meaning as commonly understood by one of skill in the art to which the invention pertains. Although any methods and materials similar herein can be used in the practice or testing of the present invention, the preferred methods and materials are described herein.

The following examples are offered by way of illustration and not by way of limitation.

EXPERIMENTAL

Example 1. Analysis of Antigen Retrieval Solutions and Incubation Temperatures

Historically, most tissue-based antigen retrieval (AR) techniques have utilized high heat, ~100° C. and/or treatment with various solutions. The AR procedure for the detection of the antigens MCM2 and MCM7 in SurePath® (TriPath Imaging, Inc.) cervical cytology samples using a cocktail of three antibodies disclosed in U.S. Pat. Nos. 7,595,380 (27C5.6 and 26H6.19 anti-MCM2 antibodies) and 7,632,498 (2E6.2 anti-MCM7 antibody), which are herein incorporated by reference in their entirety, was optimized as described hereinbelow to maintain cell morphology, while ensuring appropriate immunostaining of cytology specimens by investigating multiple AR solutions and incubation temperatures.

A broad range of potential AR (pretreatment) solutions (n=43) were tested on SurePath® cytology specimens to determine which ones would have a positive effect on immunostaining with a triple antibody cocktail (two anti-MCM2 antibodies and one anti-MCM7 antibody) that detects high-grade cervical disease. Test solutions and initial observations are grouped below:

Enzymes (e.g. pepsin, trypsin) (n=6)—degraded cellular morphology with no substantial gain in immunoreactivity.

Acids & bases (n=4)—no substantial immunoreactivity observed.

Organic solvents/miscellaneous (n=9)—no substantial immunoreactivity observed

Buffers (e.g. EDTA, citrate) and chaotropic salts (n=15)—strong chaotropic salts, especially lithium perchlorate (LiClO$_4$) alone, and in combination with some surfactants, preserved morphology and exhibited strong immunoreactivity. Others demonstrated limited gains in immunoreactivity.

Surfactants (e.g. Tween 20, Brij 35) (n=9)—most showed no substantial increase in immunostaining Sodium dodecyl sulfate (SDS) and nonyl phenoxypolyethoxylethanol (NP-40) demonstrated a moderate increase in immunostaining alone, and in combination with the activity of some chaotropic salt solutions.

Combinations of pretreatment solutions that showed promising activity were tested further. The pretreatment process that resulted in optimal MCM2/MCM7 immunostaining and cellular morphology for the SurePath® samples involves a two-step procedure, wherein the cells were first treated with 0.1% SDS, followed by an incubation with 3M LiClO$_4$/0.1% NP-40. This two-step process leverages two distinct mechanisms of antigen retrieval to boost immunoreactivity. Both SDS and NP-40 are surfactants and while not being bound by any theory or mechanism of action, it is believed the primary mechanism of action of SDS and NP-40 is to increase permeability of both the cytoplasmic membrane and the nuclear envelope. The protein targets of the triple antibody cocktail (MCM2 and MCM7) reside within the cell nucleus; therefore the primary antibody needs to cross both the cytoplasmic membrane and nuclear envelope. Increasing the permeability of these cellular structures aids in the ability of the primary antibody to penetrate both barriers and gain access to the target antigens. While not being bound by any theory or mechanism of action, it is believed the second mechanism of action of the two-solution pretreatment method is the denaturing of proteins through the use of strong protein denaturants, specifically chaotropic salts. Chaotropic salts exert this action by disrupting internal protein bonds, thus opening up protein tertiary structure and increasing the accessibility of masked target epitopes.

In the remaining experiments described hereinbelow in Example 1, the antigen retrieval process utilized Pretreatment Solution 1 (0.1% SDS) and Pretreatment Solution 2 (3M LiClO$_4$/0.1% NP-40). The optimal incubation temperature and time period for the samples with each solution was then determined.

High temperatures (greater than or equal to 80° C.) are common in most antigen retrieval procedures for tissue-based immunohistochemistry (IHC). The heat aids in breaking the cross-linking bonds caused during tissue fixation. Current methods of heating in most IHC procedures include water baths, microwave ovens and/or pressure cookers. Tissues are able to withstand these harsh AR treatments because they are fixed using solutions with formaldehyde and because tissues comprise supporting stromal cellular material that aids in the preservation of tissue architecture and cellular morphology. In contrast, cytology specimens are generally not fixed or lightly fixed and are composed of discrete cells that have no accompanying stromal support, making such samples more sensitive to standard high-temperature AR treatments. A range of AR temperatures and incubation times with AR solutions were tested to determine the temperature and time period that generates appropriate immunostaining while maintaining optimal cellular morphology.

A range of AR temperatures were investigated using the triple antibody cocktail (27C5.6 and 26H6.19 anti-MCM2 antibodies and 2E6.2 anti-MCM7 antibody) on SurePath® cervical cytology samples. An analysis of 90 cervical cytology samples incubated sequentially with Pretreatment Solution 1 and Pretreatment Solution 2 for time periods ranging from 10 to 30 minutes, and over a temperature range of 30° C. to 80° C. was carried out. All slides were evaluated by certified cytotechnologists. The percentage of abnormal cervical cells displaying immunostaining was recorded as well as the cellular morphology of each sample. The morphology was recorded on a scale of 1-3, with 1 being unacceptable (morphological degradation present) and 3 being optimal (no difference from standard AR methods). The standard AR methods that were used as a comparison in each of the experimental examples presented herein, and were also referred to herein as the "steamer method", consisted of the following steps: 1) heating a Coplin jar comprising 0.5% Sandopan LS (sodium laureth-13-carboxylate) in a steamer or water bath to greater than 95° C.; 2) submersing the slide in the heated 0.5% Sandopan LS solution for 20 minutes; and 3) removing the Coplin jar from the heat source and allowing the jar to cool for 10 minutes prior to proceeding with the immunostaining procedure.

The data indicated that all cervical samples treated with an antigen retrieval temperature of 55° C. or lower retained optimal preservation of normal cervical cellular morphology, while an antigen retrieval temperature of 80° C. resulted in degraded cervical cellular morphology (see Table 1).

TABLE 1

Assessment of cervical cell morphology following incubation with Pretreatment Solution 1 and Pretreatment Solution 2 at various temperatures.

| | Temperature | | |
| --- | --- | --- | --- |
| Grading Scale | 30° C. | 55° C. | 80° C. |
| 1 (unacceptable morphology) | 0 | 0 | 30 |
| 2 (acceptable morphology | 0 | 0 | 0 |
| 3 (optimal morphology) | 30 | 30 | 0 |
| Total cases | 30 | 30 | 30 |

Additional antigen retrieval temperature studies were carried out to investigate a focused AR temperature range from 37° C. to 60° C. These studies indicated that subtle cellular features, such as slight curling of the periphery of squamous cells, become apparent at an incubation temperature of 60° C. Table 2 contains the data from 12 matched cervical cytology specimens that were treated with AR temperatures of either 37° C. or 60° C. for one hour total. After incubation of the samples for 30 minutes at 60° C. in AR Solution 1 and 30 minutes at 60° C. in AR Solution 2, cytoplasmic folding becomes evident. Therefore, 60° C. was determined to be the upper temperature limit for incubation with antigen retrieval solutions for SurePath® samples.

TABLE 2

Antigen retrieval temperature comparison using matched cytology specimens.

| Morphology | Temperature | |
|---|---|---|
| | 37° C. | 60° C. |
| Optimal morphology | 11* | 6* |
| Cytoplasmic curling observed | 1 | 6 |
| Total | 12 | 12 |

*One case exhibited degraded white blood cells at both temperatures due to poor sample preservation. This was confirmed by the presence of degraded white blood cells on the standard SurePath ® Pap for this sample.

The upper AR temperature limit of 60° C. is not dependent upon the length of the incubation. High-grade pooled cervical specimens incubated at 60° C. for 15, 30 or 60 minutes in each of Pretreatment Solution 1 and Pretreatment Solution 2 exhibited cytoplasmic curling, while specimens incubated at either 37° C. or 42° C. for the same time periods had no morphologic degradation (see Table 3). These data support a critical design constraint of maintaining an AR temperature below 60° C. in order to ensure optimal cellular morphology that is equivalent to a standard liquid-based SurePath® Pap.

TABLE 3

Morphology of high-grade cervical pools incubated at various temperatures and time periods with pretreatment solutions.

| Incubation Time (min) | AR Temperature (° C.) | Cellular Morphology |
|---|---|---|
| 15 | 37 | Optimal |
| 15 | 42 | Optimal |
| 15 | 60 | Cytoplasmic Curling |
| 30 | 37 | Optimal |
| 30 | 42 | Optimal |
| 30 | 60 | Cytoplasmic Curling |
| 60 | 37 | Optimal |
| 60 | 42 | Optimal |
| 60 | 60 | Cytoplasmic Curling |

The AR studies demonstrate that cellular morphology can be maintained between the temperature range of 42° C. and 55° C. For additional studies using the triple antibody cocktail of two anti-MCM2 antibodies and one anti-MCM7 antibody on SurePath® samples, an AR temperature of 50° C. was selected as it resulted in optimal immunostaining and was well below the upper temperature limit of 60° C.

Example 2. Comparison of the Effects of the Two-Step Pretreatment Method with a High-Heat Pretreatment Method on Immunostaining and Morphology in Cervical Cytology Samples This study compared the two-step pretreatment method using two different chaotropic salt solutions for the second incubation step to each other and to a pretreatment method utilizing high heat (i.e., the steamer method described in Example 1).

In these experiments, SurePath® cervical cytology specimens were processed using the internally developed PrepStain Plus® Instrument (Tripath Imaging, Inc.) and deposited for staining. For those samples treated with the two-step pretreatment method, the slides were heated to 50° C. on specially-designed slide heating trays and Pretreatment Solution 1 (0.1% SDS) was applied and the slides were incubated at 50° C. for 19 minutes. The cells were washed with a standard Tris-buffered saline (TBS) solution. Pretreatment Solution 2 (either 3M $LiClO_4$/0.1% NP-40 or 3M guanidine thiocyanate/0.1% NP-40) was then added and the cells were incubated an additional 19 minutes at 50° C. Pretreatment Solution 2 (or those samples that were incubated with Pretreatment Solution 2) comprising 3M $LiClO_4$/ 0.1% NP-40 are referred to herein as $LiClO_4$ and Pretreatment Solution 2 (or those samples that were incubated with Solution 2) comprising 3M guanidine thiocyanate/0.1% NP-40 are referred to herein as GT. Following this incubation, the slides were washed again with TBS and processed for immunostaining with the MCM2/MCM7 triple antibody combination (27C5.6 and 26H6.19 anti-MCM2 antibodies and 2E6.2 anti-MCM7 antibody) and PAP counterstaining on the PrepStain Plus® instrument. The slides were then coverslipped and examined by a cytologist and/or cytopathologist.

Table 4 provides the characteristics of the 481 cervical cytology samples analyzed in these studies.

TABLE 4

Characteristics of cervical cytology samples used in these studies.

| | Biopsy | | |
|---|---|---|---|
| SP PAP | CIN 1− | CIN 2+ | Total |
| NILM | 160 | 0 | 160 |
| ASCUS | 53 | 12 | 65 |
| ASCH/AGC | 18 | 11 | 29 |
| LSIL | 57 | 36 | 93 |
| HSIL | 50 | 84 | 134 |
| Total | 338 | 143 | 481 |

SP PAP: SurePath ® Pap; NILM: negative for intraepithelial lesion or malignancy;
ASCUS: atypical squamous cells of unknown significance;
ASCH/AGC: atypical squamous cells - cannot exclude high-grade squamous intraepithelial lesion/atypical glandular cells;
LSIL: low-grade squamous intraepithelial lesion;
HSIL: high-grade squamous intraepithelial lesion;
CIN 1−: cervical intraepithelial neoplasia 1 or less;
CIN 2+: cervical intraepithelial neoplasia 2 or greater There was no statistically significant difference in terms of sensitivity or specificity or background for immune response between the $LiClO_4$ or the GT Solution 2 in samples treated using the two-step antigen retrieval method. Samples treated with guanidine thiocyanate had a 2.11% increase in sensitivity as compared to lithium perchlorate, whereas the two treatment methods resulted in the same specificity (see Table 5). More guanidine thiocyanate-treated samples had a slight background staining than those samples that had been treated with lithium perchlorate.

TABLE 5

Sensitivity and specificity of combination of two anti-MCM2 antibodies and one anti-MCM7 antibody on cervical cytology samples treated with a two-step pretreatment method comprising guanidine thiocyanate (GT) or lithium perchlorate ($LiClO_4$).

| | n | GT | $LiClO_4$ | Diff (GT − LiClO4) | 95% CI |
|---|---|---|---|---|---|
| Sensitivity | 142 | 84.51% | 82.39% | 2.11% | (−2.72%, 6.94%) |
| Specificity | 320 | 64.39% | 64.39% | 0% | (−2.62%, 2.62%) |

Diff: difference;
CI: confidence interval

When comparing those samples that had been prepared using the steamer method versus the two-step pretreatment method, there was no statistical difference in those samples that were positive or negative for immunostaining on CIN2+ cases. The data, however, showed a statistically significant difference in terms of distribution of percent cell immunopositivity. Specifically, there was an increase in cases with greater than 50% of the abnormal cells immunostaining with the steamer method versus GT (77 vs. 43) and with the steamer method vs. $LiClO_4$ (77 vs. 36) (see Tables 6 and 7).

TABLE 6

Percentage of abnormal cells immunostaining with the MCM2/MCM7 triple antibody combination on CIN2+ cervical cytology samples prepared using the steamer method or treated with a two-step pretreatment method comprising guanidine thiocyanate (GT).

| STEAMER | GT | | | | | |
|---|---|---|---|---|---|---|
| Frequency | N/A | <25% | 25%-50% | 50%-75% | >75% | Total |
| N/A | 13 | 1 | 4 | 3 | 0 | 21 |
| <25% | 2 | 6 | 4 | 0 | 0 | 12 |
| 25%-50% | 4 | 11 | 13 | 4 | 0 | 32 |
| 50%-75% | 0 | 20 | 12 | 25 | 4 | 61 |
| >75% | 2 | 4 | 3 | 5 | 2 | 16 |
| Total | 21 | 42 | 36 | 37 | 6 | 142 |

TABLE 7

Percentage of abnormal cells immunostaining with the MCM2/MCM7 triple antibody combination on CIN2+ cervical cytology samples prepared using the steamer method or treated with a two-step pretreatment method comprising lithium perchlorate ($LiClO_4$).

| STEAMER | $LiClO_4$ | | | | | |
|---|---|---|---|---|---|---|
| Frequency | N/A | <25% | 25%-50% | 50%-75% | >75% | Total |
| N/A | 14 | 3 | 2 | 2 | 0 | 21 |
| <25% | 2 | 5 | 4 | 1 | 0 | 12 |
| 25%-50% | 5 | 10 | 11 | 6 | 0 | 32 |
| 50%-75% | 2 | 18 | 21 | 18 | 2 | 61 |
| >75% | 2 | 3 | 4 | 5 | 2 | 16 |
| Total | 25 | 39 | 42 | 32 | 4 | 142 |

There was no statistically significant difference between guanidine thiocyanate-treated samples and lithium perchlorate-treated samples in terms of distribution of percent cell immunopositivity. There were more cases (121 vs. 117) with greater than 25 percent positive cells in guanidine thiocyanate-treated samples than lithium perchlorate-treated samples for CIN2+ cases (see Table 8). There was an increase in cases with >50% of the abnormal cells immunostaining in the guanidine thiocyanate-treated samples than the lithium perchlorate-treated samples (28 vs. 23) for HSIL/CIN2+ cases (see Table 9). In comparison, 14% (12/84) of HSIL/CIN2+ cases had >75% positivity when prepared using the steamer method (see Table 10).

TABLE 8

Percentage of abnormal cells immunostaining with the MCM2/MCM7 triple antibody combination on CIN2+ cervical cytology samples prepared using the two-step pretreatment method comprising either lithium perchlorate ($LiClO_4$) or guanidine thiocyanate (GT).

| | $LiClO_4$ | | | | | |
|---|---|---|---|---|---|---|
| GT | N/A | <25% | 25%-50% | 50%-75% | >75% | Total |
| N/A | 20 | 2 | 0 | 0 | 0 | 22 |
| <25% | 4 | 20 | 15 | 3 | 0 | 42 |
| 25%-50% | 2 | 12 | 15 | 6 | 1 | 36 |
| 50%-75% | 0 | 4 | 11 | 22 | 0 | 37 |
| >75% | 0 | 1 | 1 | 1 | 3 | 6 |
| Total | 26 | 39 | 42 | 32 | 4 | 143 |

TABLE 9

Percentage of abnormal cells immunostaining with the MCM2/MCM7 triple antibody combination on HSIL/CIN2+ cervical cytology samples prepared using the two-step pretreatment method comprising either lithium perchlorate ($LiClO_4$) or guanidine thiocyanate (GT).

| | $LiClO_4$ | | | | | |
|---|---|---|---|---|---|---|
| GT | N/A | <25% | 25%-50% | 50%-75% | >75% | Total |
| N/A | 6 | 0 | 0 | 0 | 0 | 6 |
| <25% | 3 | 11 | 14 | 1 | 0 | 29 |
| 25%-50% | 0 | 8 | 8 | 4 | 1 | 21 |
| 50%-75% | 0 | 2 | 9 | 14 | 0 | 25 |
| >75% | 0 | 0 | 0 | 0 | 3 | 3 |
| Total | 9 | 21 | 31 | 19 | 4 | 84 |

TABLE 10

Percentage of abnormal cells immunostaining with the MCM2/MCM7 triple antibody combination on HSIL/CIN2+ cervical cytology samples prepared using the steamer method.

| Steamer | Frequency |
|---|---|
| N/A | 5 |
| <25% | 6 |
| 25%-50% | 20 |
| 50%-75% | 41 |
| >75% | 12 |
| Total | 84 |

When examining the morphology of cervical cytology samples prepared using the steamer method or the two-step pretreatment method disclosed herein, the results showed there was a statistical difference ($p<0.0001$) in terms of the distribution of the cytology classification. Guanidine thiocyanate treatment classified 21 more ASCUS+ cases and 39 more HSIL cases than the steamer method and the lithium perchlorate treatment classified 30 more ASCUS+ cases and 52 more HSIL cases than the steamer method (see Tables 11-14).

TABLE 11

Classification of cervical cytology samples upon morphological analysis for samples prepared using the steamer method or the two-step pretreatment method comprising guanidine thiocyanate (GT).

| Steamer Frequency | GT | | | | | |
|---|---|---|---|---|---|---|
| | NILM | ASCUS | ASCH/AGC | LSIL | HSIL | Total |
| NILM | 136 | 19 | 2 | 1 | 2 | 160 |
| ASCUS | 3 | 41 | 5 | 12 | 4 | 65 |
| ASCH/AGC | 0 | 5 | 11 | 2 | 11 | 29 |
| LSIL | 0 | 3 | 0 | 58 | 30 | 91 |
| HSIL | 0 | 0 | 6 | 2 | 126 | 134 |
| Total | 139 | 68 | 24 | 75 | 173 | 479 |

*2 unsatisfactory samples in GT (i.e., insufficient number of cells present on slide to make a morphological determination)

TABLE 12

Classification of cervical cytology samples upon morphological analysis for samples prepared using the steamer method or the two-step pretreatment method comprising lithium perchlorate ($LiClO_4$).

| Steamer Frequency | $LiClO_4$ | | | | | |
|---|---|---|---|---|---|---|
| | NILM | ASCUS | ASCH/AGC | LSIL | HSIL | Total |
| NILM | 128 | 24 | 2 | 3 | 3 | 160 |
| ASCUS | 2 | 34 | 4 | 21 | 4 | 65 |
| ASCH/AGC | 0 | 4 | 11 | 2 | 12 | 29 |
| LSIL | 0 | 3 | 2 | 49 | 38 | 92 |
| HSIL | 0 | 2 | 3 | 0 | 129 | 134 |
| Total | 130 | 67 | 22 | 75 | 186 | 480 |

*1 unsatisfactory sample in $LiClO_4$

TABLE 13

Classification of CIN2+ cervical cytology samples upon morphological analysis for samples prepared using the steamer method or the two-step pretreatment method comprising guanidine thiocyanate (GT) (p = 0.0270).

| Steamer Frequency | GT | | | | |
|---|---|---|---|---|---|
| | ASCUS | ASCH/AGC | LSIL | HSIL | Total |
| ASCUS | 10 | 1 | 1 | 0 | 12 |
| ASCH/AGC | 1 | 4 | 0 | 6 | 11 |
| LSIL | 1 | 0 | 19 | 15 | 35 |
| HSIL | 0 | 2 | 1 | 81 | 84 |
| Total | 12 | 7 | 21 | 102 | 142 |

TABLE 14

Classification of CIN2+ cervical cytology samples upon morphological analysis for samples prepared using the steamer method or the two-step pretreatment method comprising lithium perchlorate ($LiClO_4$) (p = 0.0004).

| Steamer Frequency | $LiClO_4$ | | | | |
|---|---|---|---|---|---|
| | ASCUS | ASCH/AGC | LSIL | HSIL | Total |
| ASCUS | 9 | 1 | 2 | 0 | 12 |
| ASCH/AGC | 1 | 4 | 0 | 6 | 11 |
| LSIL | 2 | 1 | 13 | 19 | 35 |
| HSIL | 1 | 1 | 0 | 82 | 84 |
| Total | 13 | 7 | 15 | 107 | 142 |

Lithium perchlorate treatment identified eight more cytologically abnormal cases than guanidine thiocyanate (32 vs. 24) in 160 cases that were classified as NILM by the steamer method (see Table 15). Guanidine thiocyanate treatment classified six more ASCUS than lithium perchlorate treatment (49 vs. 43) in 319 cases that were classified as ASCUS+ by the steamer method (see Table 16). Further, among 134 cases that were classified as HSIL+ by the steamer method, lithium perchlorate treatment classified three more HSIL than guanidine thiocyanate (129 vs. 126).

TABLE 15

Classification of cervical cytology samples classified as NILM by the steamer method using the two-step pretreatment method comprising guanidine thiocyanate (GT) or lithium perchlorate ($LiClO_4$).

| GT Frequency | $LiClO_4$ | | | | | |
|---|---|---|---|---|---|---|
| | NILM | ASCUS | ASCH/AGC | LSIL | HSIL | Total |
| NILM | 126 | 9 | 0 | 1 | 0 | 136 |
| ASCUS | 2 | 15 | 0 | 2 | 0 | 19 |
| ASCH/AGC | 0 | 0 | 2 | 0 | 0 | 2 |
| LSIL | 0 | 0 | 0 | 0 | 1 | 1 |
| HSIL | 0 | 0 | 0 | 0 | 2 | 2 |
| Total | 128 | 24 | 2 | 3 | 3 | 160 |

TABLE 16

Classification of cervical cytology samples classified as ASCUS+ by the steamer method using the two-step pretreatment method comprising guanidine thiocyanate (GT) or lithium perchlorate ($LiClO_4$).

| GT Frequency | $LiClO_4$ | | | | | |
|---|---|---|---|---|---|---|
| | NILM | ASCUS | ASCH/AGC | LSIL | HSIL | Total |
| NILM | 2 | 1 | 0 | 0 | 0 | 3 |
| ASCUS | 0 | 38 | 2 | 9 | 0 | 49 |
| ASCH/AGC | 0 | 2 | 17 | 2 | 1 | 22 |
| LSIL | 0 | 2 | 1 | 58 | 13 | 74 |
| HSIL | 0 | 0 | 0 | 2 | 169 | 171 |
| Total | 2 | 43 | 20 | 71 | 183 | 319 |

*2 unsatisfactory samples in GT

Overall, guandine thiocyanate and lithium perchlorate treatment did not degrade cellular morphology as compared to the steamer method. Further, glandular cells and atrophic samples treated with the two-step pretreatment method exhibit less immunostaining than those processed using the steamer method. The two-step antigen retrieval method did not reduce immune/clinical performance as compared to the steamer method, although there was a reduction observed in the percentage of cells that were immunopositive compared to those samples processed with the steamer method. For N1LM and CIN2 confirmed cases, the two-step pretreatment method upgraded the cytological classification.

Figure 2:
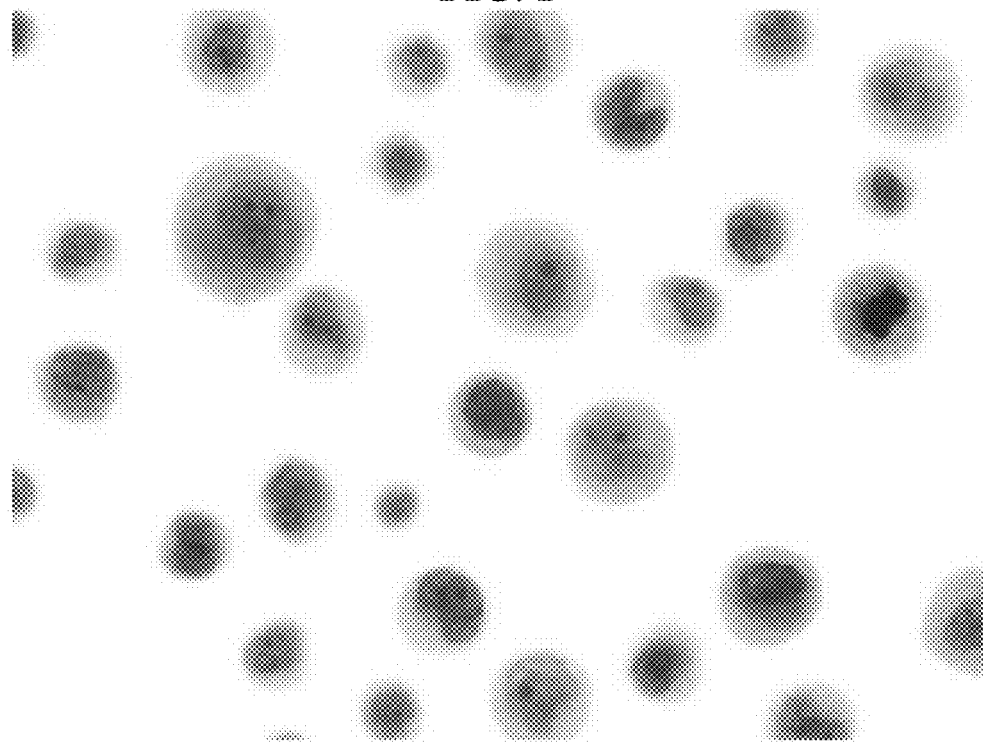
FIG. 2 provides an image of SiHa (human cervical squamous cancer) cells immunostained with an anti-Ki67 antibody. Prior to immunostaining, the cells were incubated at 50° C. for 19 minutes in 0.1% SDS, washed in TBS, and then incubated at 50° C. for 19 minutes in 3M $LiClO_4$/0.1% NP-40. The cells were counterstained with Pap stain.
Figure 3:
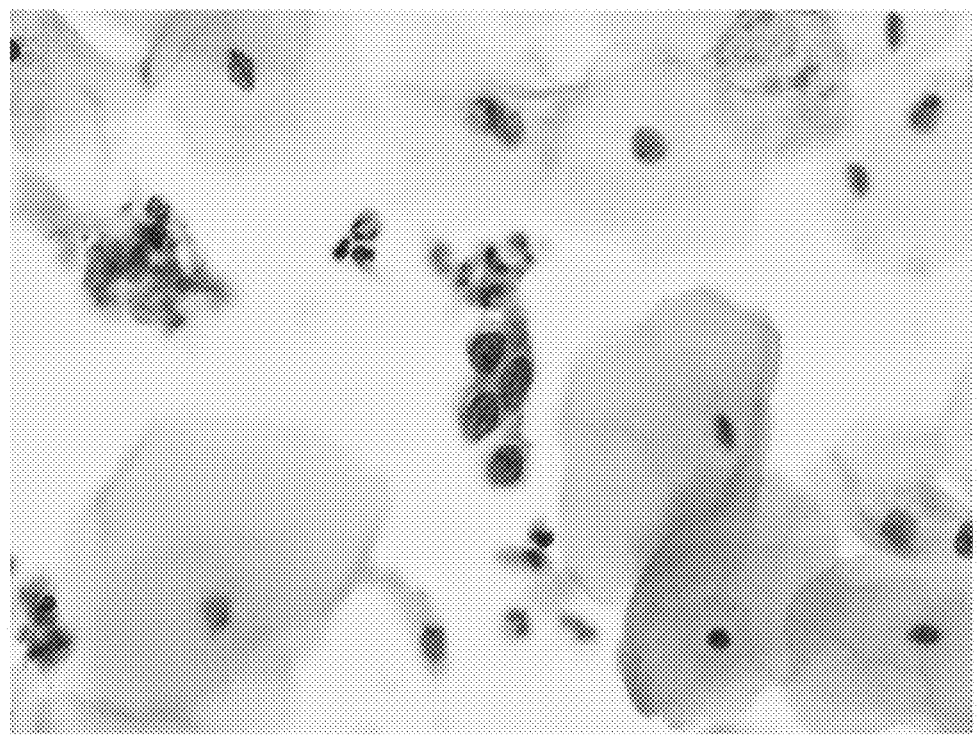
FIG. 3 provides an image of a SurePath® HSIL cervical cytology sample immunostained with an anti-p16 antibody. Prior to immunostaining, the sample was incubated at 50° C. for 19 minutes in 0.1% SDS, washed in TBS, and then incubated at 50° C. for 19 minutes in 3M $LiClO_4$/0.1% NP-40. The sample was counterstained with Pap stain.
Figure 4:
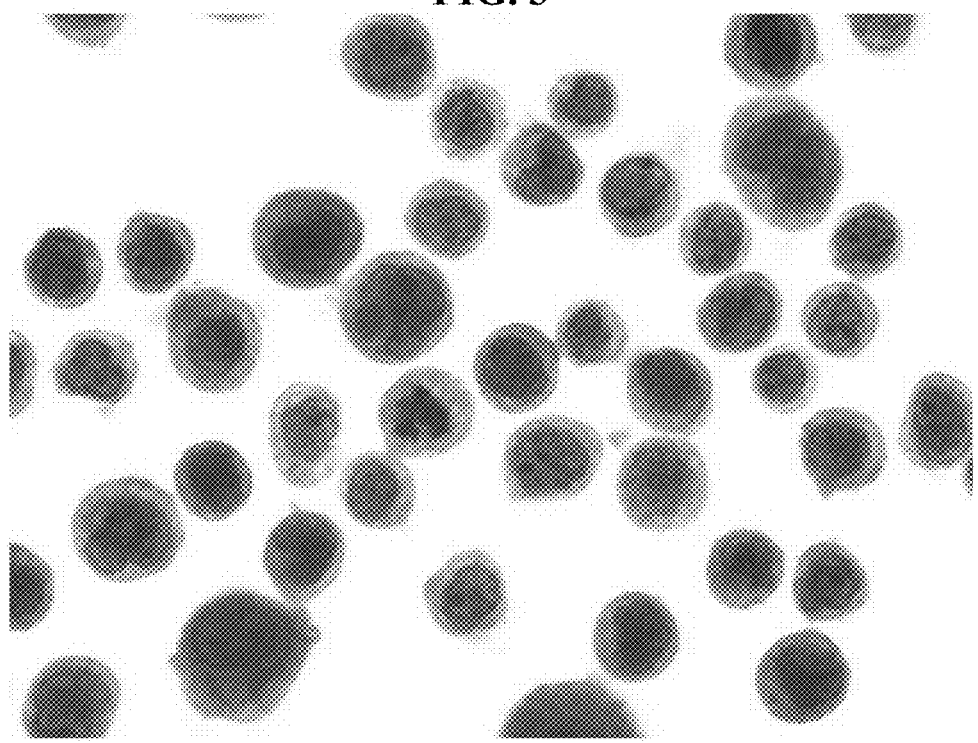
FIG. 4 provides an image of SiHa cells immunostained with an anti-p16 antibody. Prior to immunostaining, the cells were incubated at 50° C. for 19 minutes in 0.1% SDS, washed in TBS, and then incubated at 50° C. for 19 minutes in 3M $LiClO_4$/0.1% NP-40. The cells were counterstained with Pap stain.

Example 3. Detection of Antigens Ki67 and p16 in Cervical Cytology Samples Using the Two-Step Pretreatment Process In these experiments, SurePath® cervical cytology specimens were processed using the internally developed PrepStain Plus® Instrument (Tripath Imaging, Inc.) and deposited for staining. Following cell deposition, the slides were heated to 50° C. on specially-designed slide heating trays and AR Solution 1 (0.1% SDS) was applied and the slides were incubated at 50° C. for 19 minutes. The cells were washed with a standard tris-buffered saline (TBS) solution. AR Solution 2 (3M LiClO$_4$/0.1% NP-40) was then added and the cells were incubated an additional 19 minutes at 50° C. Following this incubation, the slides were washed again with TBS and processed for immunostaining and PAP counterstaining on the PrepStain Plus® instrument. The slides were then coverslipped and examined by a cytologist and/or cytopathologist. Representative results of cervical cytology samples immunostained with an anti-Ki67 or anti-p16 antibody are shown in FIGS. 1 and 3, respectively. SiHa cells were treated similarly and immunostained with an anti-Ki67 (FIG. 2) or anti-p16 antibody (FIG. 4).

Figure 5:
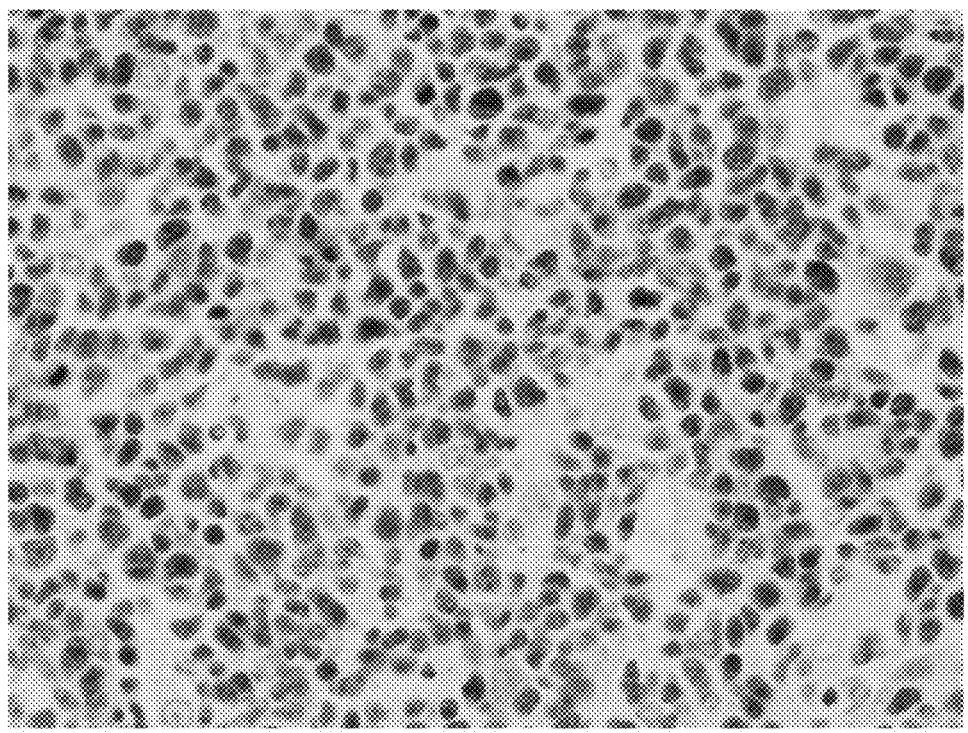
FIG. 5 provides an image of a histological section of paraffin-embedded tonsil tissue immunostained with two anti-MCM2 antibodies and one anti-MCM7 antibody. The tonsil tissue had been fixed in 10% formaldehyde for at least 24 hours and then embedded in paraffin before sectioning. Prior to immunostaining, the section was incubated at 50° C. for 19 minutes in 0.1% SDS, washed in TBS, and then incubated at 50° C. for 19 minutes in 3M $LiClO_4$/0.1% NP-40.
Figure 6:
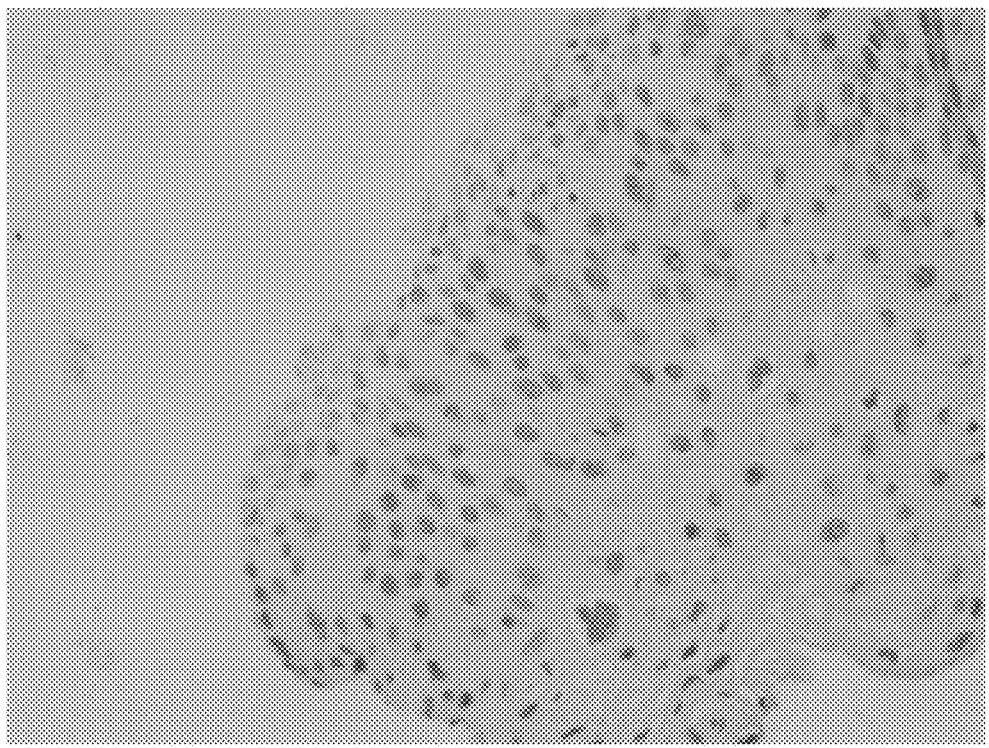
FIG. 6 provides an image of a histological section of paraffin-embedded cervical intraepithelial neoplasia 3 (CIN3) tissue immunostained with two anti-MCM2 antibodies and one anti-MCM7 antibody. The cervical tissue had been fixed in 10% formaldehyde for at least 24 hours and then embedded in paraffin before sectioning. Prior to immunostaining, the section was incubated at 50° C. for 19 minutes in 0.1% SDS, washed in TBS, and then incubated at 50° C. for 19 minutes in 3M $LiClO_4$/0.1% NP-40.

Example 4. Detection of MCM2 and MCM7 in Tonsil and Cervical Tissues Using the Two-Step Pretreatment Process Tonsil and cervical tissue samples were fixed in 10% formaldehyde for at least 24 hours and then embedded in paraffin before sectioning. Tissue sections were incubated with Solution 1 (0.1% SDS) at 50° C. for 19 minutes. The sections were washed with TBS and then incubated at 50° C. for 19 minutes in Solution 2 (3M LiClO$_4$/0.1% NP-40). Following this incubation, the tissue sections were washed again with TBS and processed for immunostaining with a triple antibody cocktail (27C5.6 and 26H6.19 anti-MCM2 antibodies and 2E6.2 anti-MCM7 antibody) and PAP counterstaining on the PrepStain Plus® Instrument. Representative immunostained tonsil and cervical tissues are shown in FIGS. 5 and 6, respectively. These results demonstrate that the two-step pretreatment process disclosed herein can effectively retrieve antigens from histological samples, resulting in efficient immunostaining.

Example 5. Detection of Nuclear Antigens in Cervical Cells Using the Two-Step Pretreatment Process in the Absence of Heat SurePath® low-grade squamous intraepithelial lesion (LSIL) and high-grade squamous intraepithelial lesion (HSIL) cervical cytology specimens were processed as described in Example 3 for antigen retrieval by incubating the samples in Pretreatment Solution 1 (0.1% SDS) for 19 minutes, followed by washing with TBS, and incubation in Pretreatment Solution 2 (3M LiClO$_4$/0.1% NP-40) for 19 minutes. In contrast to the experiments described in Example 3, however, no exogenous heat was applied to the samples during the incubation steps with the two pretreatment solutions. Therefore, the incubation steps with Pretreatment Solutions 1 and 2 were performed at room temperature.

Figure 7:
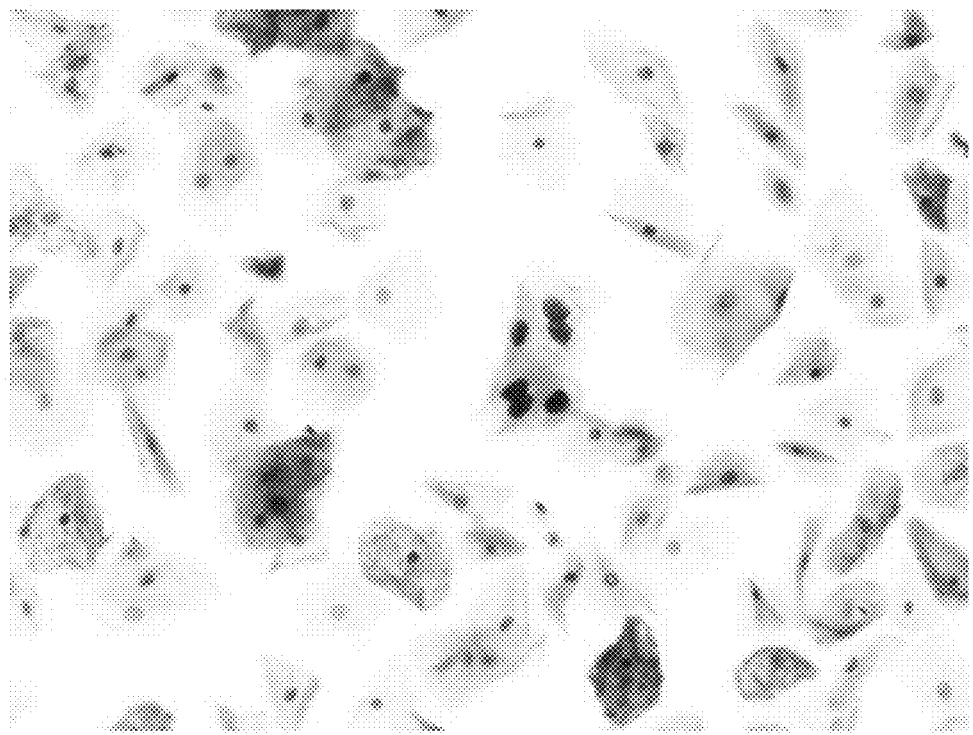
FIG. 7 provides an image of a SurePath® low-grade squamous intraepithelial lesion (LSIL) cervical cytology sample immunostained with two anti-MCM2 antibodies and one anti-MCM7 antibody. Prior to immunostaining, the sample was incubated at room temperature for 19 minutes in 0.1% SDS, washed in TBS, and then incubated at room temperature for 19 minutes in 3M $LiClO_4$/0.1% NP-40. The sample was counterstained with Pap stain.
Figure 8:
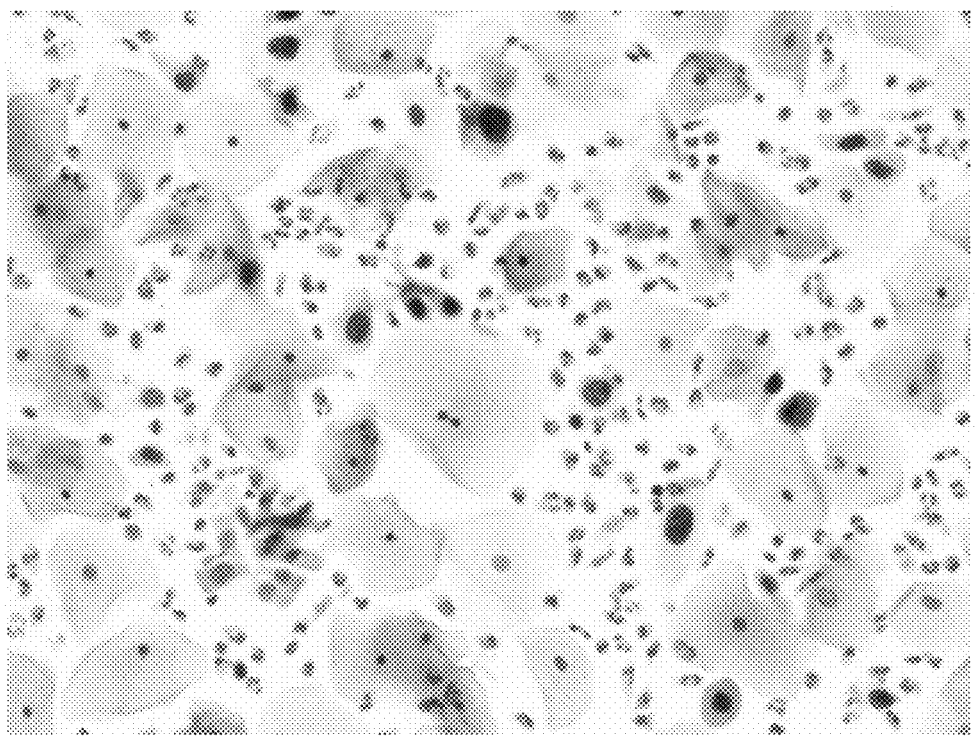
FIG. 8 provides an image of a SurePath® high-grade squamous intraepithelial lesion (HSIL) cervical cytology sample immunostained with two anti-MCM2 antibodies and one anti-MCM7 antibody. Prior to immunostaining, the sample was incubated at room temperature for 19 minutes in 0.1% SDS, washed in TBS, and then incubated at room temperature for 19 minutes in 3M $LiClO_4$/0.1% NP-40. The sample was counterstained with Pap stain.

Following pretreatment, the samples were immunostained with a triple antibody cocktail (27C5.6 and 26H6.19 anti-MCM2 antibodies and 2E6.2 anti-MCM7 antibody) and PAP counterstained. Representative samples are shown in FIG. 7 (LSIL) and FIG. 8 (HSIL). These data demonstrate the unexpected effect of the presently disclosed two-step pretreatment method to effectively expose epitopes while maintaining cellular morphology of cytology samples, even in the absence of applied heat.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the foregoing list of embodiments and appended claims. Although specific terms are employed herein, they are used in a generic and descriptive sense only and not for purposes of limitation.

That which is claimed:

1. A method for preparing a cytology sample for immunological staining, said method comprising:
   a) providing a cytology sample wherein the cytology sample is a patient sample disposed in a liquid cytology medium comprising formaldehyde, methanol, ethanol and isopropanol onto a microscope slide wherein said patient sample comprises cells or tissues;
   b) incubating the cytology sample for at least a minute and less than an hour with a first solution comprising a surfactant at room temperature while the cytology sample remains disposed on the microscope slide;
   c) incubating the cytology sample for at least a minute and less than an hour with a second solution comprising a chaotropic agent and a weak surfactant at room temperature while the cytology sample remains disposed on the microscope slide;
   d) following steps a)-c), immunologically staining the cytology sample;
   e) Papanicolaou (Pap) staining of the cytology sample; and
   f) performing a morphological analysis of said cytology sample;
   wherein step c) follows step b), and wherein said method allows for immunological staining of nuclear antigens, wherein a morphology of the patient sample is preserved.

2. The method of claim 1, wherein said surfactant of said first solution is an anionic surfactant.

3. The method of claim 2, wherein said anionic surfactant is sodium dodecyl sulfate (SDS).

4. The method of claim 3, wherein said first solution comprises about 0.1% SDS.

5. The method of claim 1, wherein said chaotropic agent is a chaotropic salt.

6. The method of claim 5, wherein said chaotropic salt is a thiocyanate or perchlorate.

7. The method of claim 6, wherein said thiocyanate is guanidine thiocyanate.

8. The method of claim 7, wherein said second solution comprises about 3M guanidine thiocyanate.

9. The method of claim 6, wherein said perchlorate is lithium perchlorate.

10. The method of claim 9, wherein said second solution comprises about 3M lithium perchlorate.

11. The method of claim 1, wherein said weak surfactant of said second solution is nonyl phenoxypolyethoxylethanol (NP-40).

12. The method of claim 11, wherein said second solution comprises about 0.1% NP-40.

13. The method of claim 1, where said cytology sample is incubated with said first solution for about 19 minutes.

14. The method of claim 1, where said cytology sample is incubated with said second solution for about 19 minutes.

15. The method of claim 1, wherein said cytology sample is washed prior to contacting the cytology sample with the second solution and after contacting the sample with the first solution.

16. The method of claim 1, wherein said method further comprises staining and detecting at least one nuclear antigen in said cytology sample using an antibody.

17. The method of claim 1, further comprises staining and detecting at least one antigen wherein said antigen is at least one nuclear antigen selected from the group consisting of MCM2 and MCM7 or at least one antigen selected from the group consisting of p16, and Ki67.

18. The method of claim 1, wherein said patient sample is a cervical sample.

\* \* \* \* \*